(12) United States Patent
Grenon et al.

(10) Patent No.: US 8,600,484 B2
(45) Date of Patent: *Dec. 3, 2013

(54) MEIBOMIAN GLAND IMAGING

(75) Inventors: Stephen M. Grenon, Durham, NC (US); Timothy R. Willis, Raleigh, NC (US); Benjamin T. Gravely, Raleigh, NC (US); Donald R. Korb, Boston, MA (US)

(73) Assignee: TearScience, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,654

(22) Filed: May 16, 2012

(65) Prior Publication Data

US 2012/0226156 A1 Sep. 6, 2012

Related U.S. Application Data

(63) Continuation of application No. 11/540,422, filed on Sep. 29, 2006, now Pat. No. 8,249,695.

(51) Int. Cl.
*A61B 6/00* (2006.01)

(52) U.S. Cl.
USPC ............ 600/476; 600/407; 600/452; 600/473

(58) Field of Classification Search
USPC ......... 600/407, 427, 437, 452, 473–474, 476; 607/1
See application file for complete search history.

(56) References Cited

U.S. PATENT DOCUMENTS

| | | | |
|---|---|---|---|
| 3,909,771 A | 9/1975 | Pickering et al. | |
| RE28,873 E | 6/1976 | Morgan | |
| 4,261,364 A | 4/1981 | Haddad et al. | |
| 4,274,421 A | 6/1981 | Dory | |
| 4,567,898 A | 2/1986 | Plugge et al. | |
| 4,584,880 A | 4/1986 | Matzuk | |
| 5,137,355 A * | 8/1992 | Barbour et al. | ............... 356/342 |
| 5,557,351 A | 9/1996 | Kasahara et al. | |
| 5,621,523 A | 4/1997 | Oobayashi et al. | |
| 5,958,912 A | 9/1999 | Sullivan et al. | |
| 5,993,391 A | 11/1999 | Kamiyama | |

(Continued)

FOREIGN PATENT DOCUMENTS

EP 2189108 A1 5/2010
JP 2002515593 A 5/2002

(Continued)

OTHER PUBLICATIONS

Hyrnchak, P. 'Optical Coherence Tomography: An Introduction to the Technique and its Use', Optometry and Vision Science, vol. 77, No. 7, Jul. 2000.*

(Continued)

*Primary Examiner* — James Kish
*Assistant Examiner* — Daniel Huntley
(74) *Attorney, Agent, or Firm* — Withrow & Terranova, PLLC

(57) ABSTRACT

A method of evaluating dry eye in humans wherein the flow of naturally occurring secretion to the eye is reduced or stopped due to the presence of an obstruction of a meibomian gland in the eyelid involves applying a pressure to the eyelid that mimics pressure applied during blinking; and simultaneously imaging the glands to diagnose the condition of the meibomian gland. This abstract is not to be considered limiting, since other embodiments may deviate from the features described in this abstract.

38 Claims, 23 Drawing Sheets

(56) References Cited

U.S. PATENT DOCUMENTS

| | | | |
|---|---|---|---|
| 6,024,095 | A | 2/2000 | Stanley, III |
| 6,072,180 | A | 6/2000 | Kramer et al. |
| 6,107,289 | A | 8/2000 | Sullivan |
| 6,153,607 | A | 11/2000 | Pflugfelder et al. |
| 6,228,029 | B1 | 5/2001 | Eccardt et al. |
| 6,419,361 | B2 * | 7/2002 | Cabib et al. ................ 351/221 |
| 6,455,583 | B1 | 9/2002 | Pflugfelder et al. |
| 6,500,123 | B1 | 12/2002 | Holloway et al. |
| 6,556,853 | B1 | 4/2003 | Cabib et al. |
| 6,743,249 | B1 | 6/2004 | Alden |
| 6,949,071 | B1 * | 9/2005 | Saied et al. ................ 600/445 |
| 7,060,061 | B2 | 6/2006 | Altshuler et al. |
| 7,111,980 | B2 * | 9/2006 | Pavlidis et al. ............. 374/45 |
| 7,118,217 | B2 | 10/2006 | Kardon et al. |
| 7,281,801 | B2 * | 10/2007 | Wang ........................ 351/246 |
| 2002/0180929 | A1 | 12/2002 | Tseng et al. |
| 2003/0018271 | A1 | 1/2003 | Kimble |
| 2003/0067249 | A1 | 4/2003 | Lockwood et al. |
| 2003/0069489 | A1 | 4/2003 | Abreu |
| 2003/0114426 | A1 | 6/2003 | Pflugfelder et al. |
| 2003/0195438 | A1 | 10/2003 | Petillo |
| 2003/0211043 | A1 | 11/2003 | Korb |
| 2003/0233135 | A1 | 12/2003 | Yee |
| 2004/0001203 | A1 | 1/2004 | Simpson |
| 2004/0238969 | A1 | 12/2004 | Chen |
| 2005/0203421 | A1 | 9/2005 | Zeng et al. |
| 2006/0106283 | A1 | 5/2006 | Wallace et al. |
| 2006/0109423 | A1 | 5/2006 | Wang |
| 2006/0173360 | A1 | 8/2006 | Kalafut et al. |
| 2006/0187462 | A1 | 8/2006 | Srinivasan et al. |
| 2006/0223032 | A1 | 10/2006 | Fried et al. |
| 2011/0273550 | A1 | 11/2011 | Amano et al. |

FOREIGN PATENT DOCUMENTS

| | | | |
|---|---|---|---|
| JP | 2004236727 A * | 8/2004 | |
| JP | 2004536653 A | 12/2004 | |
| JP | 2006198249 A | 8/2006 | |
| JP | 2009134276 A | 6/2009 | |
| KR | 101259056 B1 | 4/2013 | |
| WO | 9958131 A1 | 11/1999 | |
| WO | 9960331 A1 | 11/1999 | |
| WO | 03011135 A1 | 2/2003 | |
| WO | 2004041134 A1 | 5/2004 | |
| WO | 2012137545 A1 | 10/2012 | |

OTHER PUBLICATIONS

Goto, E. et al., Treatment of non-inflamed obstructive meibomian gland dysfunction by an infrared warm compression device. British Journal of Ophthalmology 2002; 86:1403-1407.*

Korb, D. et al., 'Increase in Tear Film Lipid Layer Thickness Following Treatment for Meibomian Gland Dysfunction', Advances in Experimental Medicine and Biology, 1994; 350:293-298.*

Komuro, Aoi, 'Examination of the Meibomian Gland', Journal of the Eye, vol. 18, issue 3, 2001. Full Translation, pp. 1-28, translated on Jun. 25, 2012.*

Alsuhaibani, Adel et al. "Utility of Meibography in the Evaluation of Meibomian Glands Morphology in Normal and Diseased Eyelids," Saudi Journal of Ophthalmology, vol. 25, No. 1, Jan.-Mar. 2011, pp. 61-66.

Korb, Donald R., O.D., et al., "Meibomian Gland Dysfunction and Contact Lens Intolerance" Journal of the American Optometric Association, vol. 51 No. 3, Mar. 1980, pp. 243-251.

Mansour, Ahmad M., "Meibomian Gland Secretion" Orbit: The International Journal on Orbital Disorders, Oculoplastic and Lacrimal Surgery, vol. 7 Iss. 3, Sep. 1988, pp. 201-209, (Abstract Only).

Korb, Donald R. et al., "Lid Wiper Epitheliopathy and Dry Eye Symptoms," Eye & Contact Lens, vol. 31, No. 1, Jan. 2005, pp. 2-8.

Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).

Mitra, M. et al., "Tear Film Lipid Layer Thickness and Ocular Comfort after Meibomian Therapy via Latent Heat with a Novel Device in Normal Subjects," Eye, vol. 19, 2005, pp. 657-660.

Matsuoka, Tooru et al., "Value of Meibography of the Upper Eyelid in Meibomian Gland Dysfunction," Japanese Journal of Clinical Ophthalmology, vol. 53 No. 3, Oct. 1998, pp. 389-393, (Abstract Only).

Bucsko, J.K., "Imaging the Eye with Very-High-Frequency Ultrasound," Radiology Today, vol. 5 No. 19, Sep. 13, 2004, 4 pages.

Arcscan, "Product Description," ArcScan, Accessed Jan. 9, 2008, 5 pages, http://www.arcscan.com/products.html.

Visual Sonics, "Inflammation Quantified in Vivo," VisualSonics, Accessed Jan. 9, 2008, 2 pages, http://www.visualsonics.com/.

Paradigm, "P45," Paradigm Medical, Accessed Jan. 9, 2008, 2 pages, http://web.archive.org/web/20060207051154/http://paradigm-medical.com/products/P45.htm.

OTI Ophthalmic Technologies, Inc., "OCT/SLO Technical Specifications," OTI Ophthalmic Technologies Inc., Accessed Jan. 9, 2008, 2 pages, http://web.archive.org/web/20051108020036/http://www.oti-canada.com/octspecs.htm.

Quantel Medical, "New Ophthalmic Products," Quantel Medical Ophthalmic Products, Accessed Jan. 9, 2008, 4 pages, http://web.archive.org/web/20060221081738/http://quantelmedical.com/index.htm.

Van Velthoven, M. et al., "Overlay of Conventional Angiographic and en-face OCT Images Enhances their Interpretation," BMC Ophthalmology, vol. 5 No. 12, Jun. 2005, 13 pages.

Stratus OCT, "Vision of Technology," Stratus OCT, 2002, 6 pages.

Arndt, G. et al., "Microwave Treatment of Prostate Cancer and Hyperplasia," NASA Tech Brief, Jun. 2005, pp. 62.

King-Smith, P. et al., "The Thickness of the Human Precorneal Tear Film: Evidence from Reflection Spectra," Investigative Ophthalmology and Visual Science, vol. 41 No. 11, Oct. 2000, pp. 3348-3359.

Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.

Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).

Notice of Allowance for U.S. Appl. No. 11/540,422 mailed Jun. 21, 2012, 9 pages.

Non-final Office Action for U.S. Appl. No. 11/540,422 mailed Aug. 31, 2011, 14 pages.

Final Office Action for U.S. Appl. No. 11/540,422 mailed Jul. 20, 2010, 11 pages.

Non-final Office Action for U.S. Appl. No. 11/540,422 mailed Dec. 30, 2009, 11 pages.

Non-final Office Action for U.S. Appl. No. 11/540,422 mailed Apr. 15, 2009, 10 pages.

Notice of Allowance for U.S. Appl. No. 11/893,669 mailed Apr. 26, 2012, 7 pages.

Final Office Action for U.S. Appl. No. 11/893,669 mailed Feb. 15, 2012, 21 pages.

Non-final Office Action for U.S. Appl. No. 11/893,669 mailed Jun. 9, 2011, 21 pages.

Non-final Office Action for U.S. Appl. No. 13/325,586 mailed Jul. 5, 2012, 8 pages.

International Search Report for PCT/US07/00505 mailed Nov. 20, 2007, 10 pages.

Office Action for Japanese patent application 2009-530326 mailed Apr. 3, 2012, 6 pages.

Komuro, A. et al., "Examination of the Meibomian Gland," New Ophthalmology, vol. 18, No. 3, Mar. 31, 2001, pp. 301-306 (Japanese version and partial translation).

Millar, et al., "Analysis of comparison of human meibomian lipid films and mixtures with cholesteryl esters in vitro films using high resolution color microscopy," Cornea, vol. 53, No. 8, Jul. 2012, pp. 4710-4719.

Messmer et al., "Konfokale in-vivo-mikroskopie bei Blepharitis," Klin. Monatsbl. Augenheilkund., vol. 222, 2005, pp. 894-900.

(56) References Cited

OTHER PUBLICATIONS

Robin et al., "In vivo transillumination biomicroscopy and photography of meibomian gland dysfunction," Ophthalmology, vol. 92, No. 10, Oct. 1985, pp. 1423-1426.

Yamaguchi et al., "Marx line: fluorescein staining line on the inner lid as indicator of meibomian gland function," American Journal of Ophthalmology, vol. 141, No. 4, Apr. 1, 2006, pp. 669-669.

Supplementary European Search Report for application 07716444 mailed Oct. 4, 2012, 4 pages.

Translation of the 2nd Official Action for Japanese patent application 2009-530326 mailed Mar. 26, 2013, 6 pages.

Agnifili et al., "In vivo confocal microscopy of meibomian glands in glaucoma," British Journal of Ophthalmology, vol. 97, No. 3, Mar. 2013, pp. 343-349, United Kingdom.

Yokoi et al., "A Newly Developed Video-Meibography System Featuring a Newly Designed Probe," Japan Journal of Ophthalmology, vol. 51, Jan. 2007, pp. 53-56.

Final Office Action for U.S. Appl. No. 13/325,586 mailed Feb. 12, 2013, 11 pages.

Non-final Office Action for U.S. Appl. No. 13/325,586 mailed Jun. 25, 2013, 12 pages.

\* cited by examiner

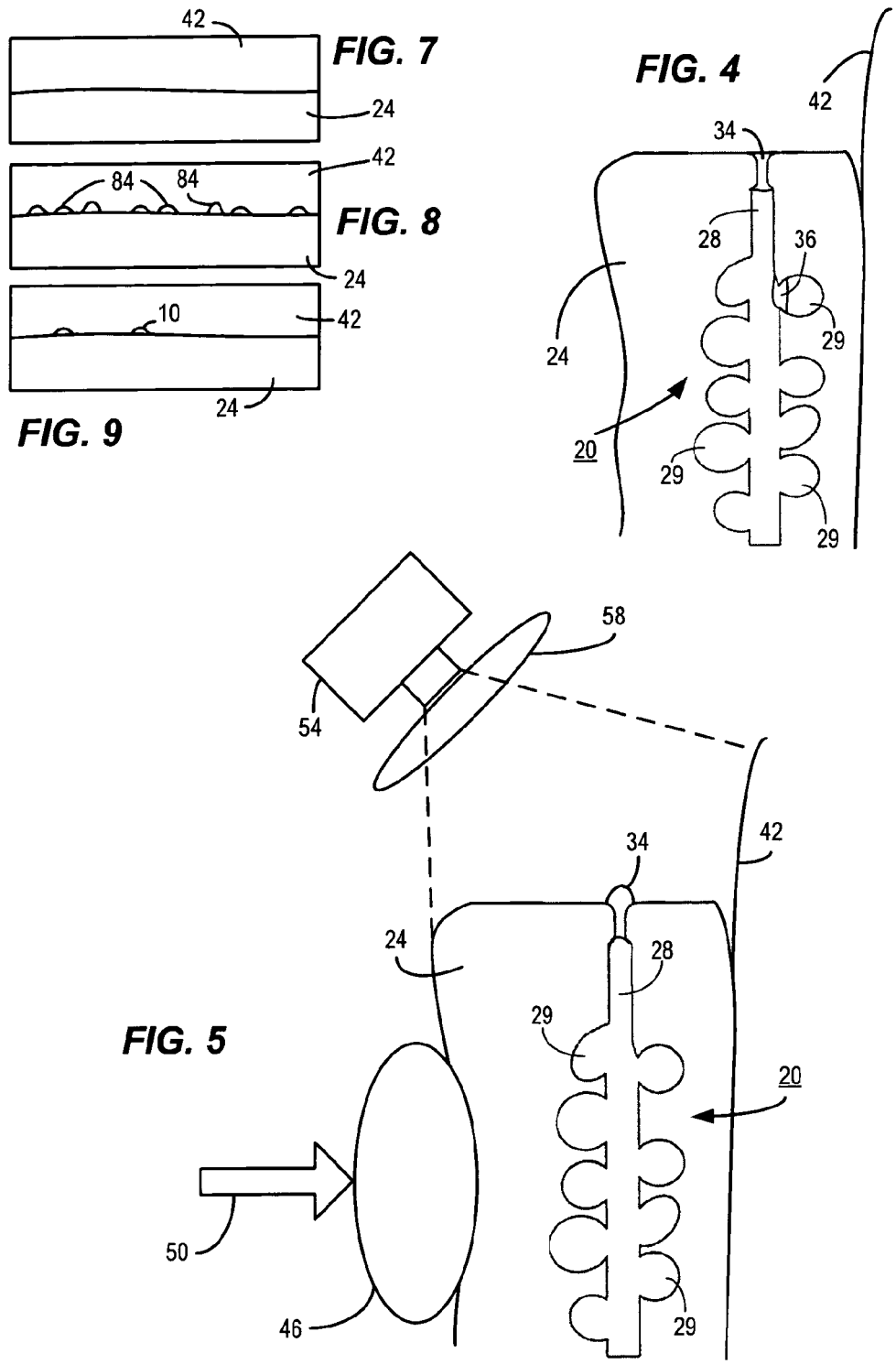

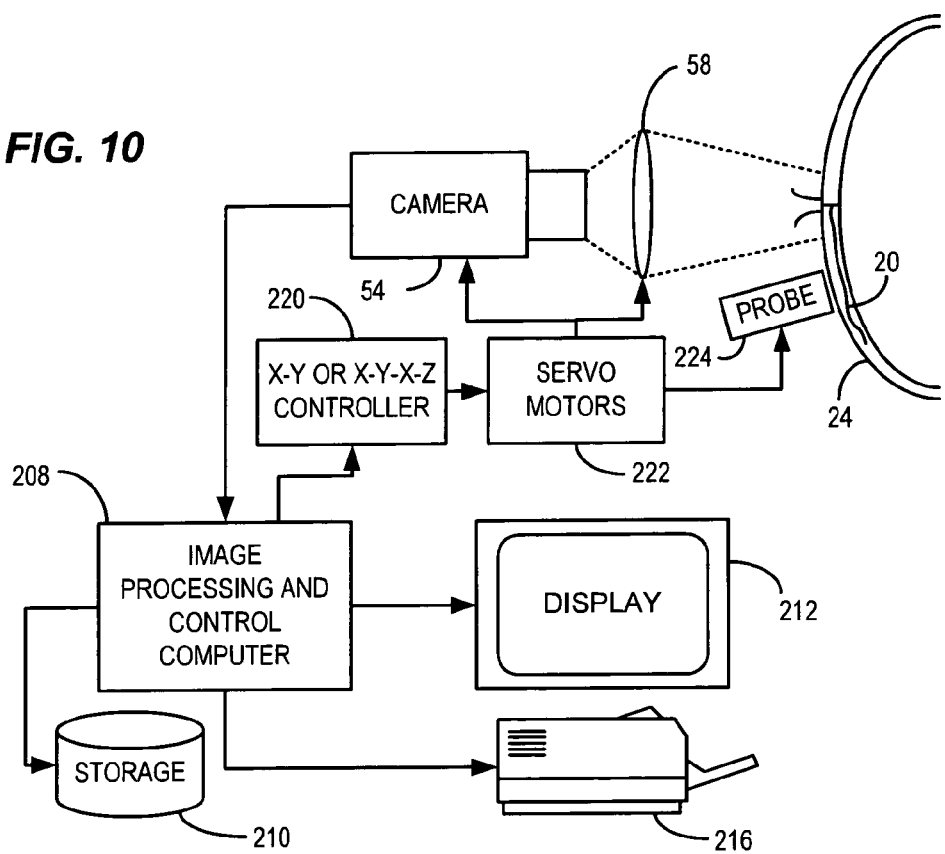

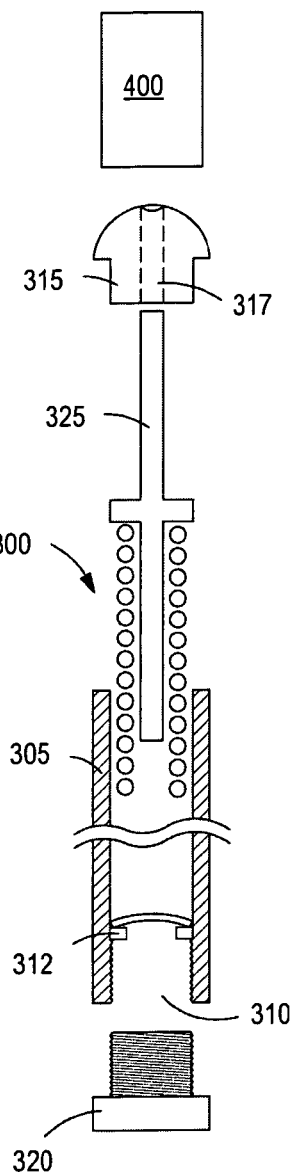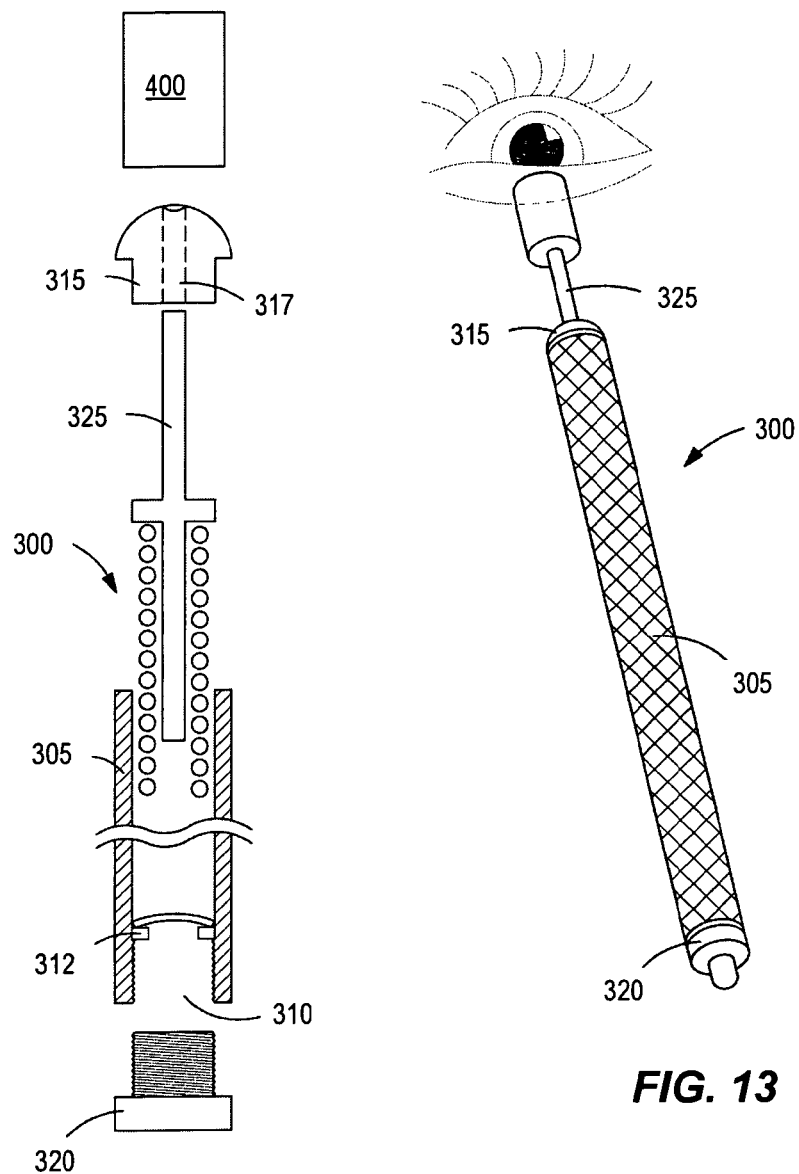
FIG. 14
FIG. 13

MEIBOMIAN GLAND IMAGING

RELATED APPLICATIONS

The present application is a continuation application of U.S. patent application Ser. No. 11/540,422, filed Sep. 29, 2006, entitled "Meibomian Glad Imaging," which is incorporated herein by reference in its entirety.

FIELD

This invention relates generally to the field of imaging of eyelids of mammals. In particular, certain embodiments consistent with the invention relate to imaging of mammalian meibomian glands (also known as tarsal glands) of the eye including imaging of the meibomian glands to determine a degree of secretory function, dysfunction obstruction, diagnosis or effectiveness of treatment of such glands.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located on both the upper and lower eye lids, with orifices designed to discharge the lipid secretions onto the lid margins, thus forming the lipid layer of the tear film. The typical upper eyelid has about 25 meibomian glands and the lower eyelid has about 20 meibomian glands, which are somewhat larger than those located in the upper lid. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the lid margin at and around the junction of the inner mucous membrane and the outer skin of the eyelids termed the mucocutaneous junction.

Specifically, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

Blinking causes the upper lid to pull a sheet of the lipids secreted by the meibomian glands over the other two layers of the tear film, thus forming a type of protective coating which limits the rate at which the underlying layers evaporate. Thus, it will be seen that a defective lipid layer or an incorrect quantity of such lipids can result in accelerated evaporation of the aqueous layer which, in turn, causes symptoms such as itchiness, burning, irritation, and dryness, which are collectively referred to as "dry eye".

Dry eye states have many etiologies. A common cause of common dry eye states is the condition known as "meibomian gland dysfunction" (MGD), a disorder where the glands are obstructed or occluded. A common cause of common dry eye states is a disorder where the glands are obstructed or occluded, usually referred to as "meibomian gland dysfunction" (MGD). As employed herein the terms "occluded" and "obstruction" as they relate to meibomian gland dysfunction are defined as partially or completely blocked or plugged meibomian glands, or any component thereof, having a solid, semi-solid or thickened congealed secretion and/or plug, leading to a compromise, or more specifically, a decrease or cessation of secretion. Also with a reduced or limited secretion the meibomian gland may be compromised by the occluded or obstructive condition as evidenced by a yellowish color indicating a possible infection state, or may be otherwise compromised so that the resulting protective lipid protective film is not adequate.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions can comprise combination of bacteria, sebaceous ground substance, dead, and/or desquamated epithelial cells, see, Korb et al., Meibomian Gland Dysfunction and Contact Lens Intolerance, Journal of the Optometric Association, Vol. 51, Number 3, (1980), pp. 243-251. While meibomitis is obvious by inspection of the external lids, meibomian gland dysfunction may not be obvious even when examined with the magnification of the slit-lamp biomicroscope, since there may not be external signs or the external signs may be so minimal that they are overlooked. The external signs of meibomian gland dysfunction without obvious lid inflammation may be limited to subtle alterations of the meibomian gland orifices, overgrowth of epithelium over the orifices, and pouting of the orifices of the glands with congealed material acting as obstructions. In severe instances of meibomian gland dysfunction without obvious lid inflammation the changes may be obvious, including serrated or undulated lid margins, orifice recession and more obvious overgrowth of epithelium over the orifices, and pouting of the orifices.

Hormonal changes, which occur during menopause, and particularly changing estrogen levels, can result in thickening of the oils secreted by the meibomian glands which results in clogged gland orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice thus further restricting sebum flow and exacerbating the dry eye condition. Additional factors which may cause or exacerbate meibomian gland dysfunction include, age, disorders of blinking, activities such as computer use which compromise normal blinking, contact lens wear and hygiene, cosmetic use, or other illness, particularly diabetes.

The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained (see Korb, et al., "Increase in Tear Film Lipid Layer Thickness Following Treatment of Meibomian Gland Dysfunction", Lacrimal Gland, tear Film, ad Dry Eye Syndromes, pp. 293-298, Edited by D.A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye".

While the tear film operates as a singular entity and all of the layers thereof are important, the lipid layer, which is secreted from the meibomian glands, is of particular significance as it functions to slow the evaporation of the underlying layers and to lubricate the eyelid during blinking which prevents dry eye.

Thus, to summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome". While not the only cause, meibomian gland dysfunction (MGD) is known to be a major cause of dry eye syndrome. The disorder is characterized by a blockage of some sort within the meibomian glands or at their surface preventing normal lipid secretions from flowing from the meibomian glands to form the lipid layer of the tear film.

Such secretions serve to prevent evaporation of the tear film and lubricate the eye and eyelids, hence their absence can cause dry eye syndrome. Obstructions or occlusions of the meibomian glands may be present over or at the orifice of the gland, in the main channel of the gland which may be narrowed or blocked, or possibly in other locations including the passages from the acini to the main channel.

It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe® and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in United States Patent Publication no. US2003/011426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover) to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in Keratoconjuctivitis Sicca as disclosed in U.S. Pat. No. 5,958,912 and U.S. Pat. No. 6,107,289 both titled "Ocular Therapy in Keratoconjunctivitis Sicca Using Topically Applied Androgens or TGF-β" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely.

One modality for the heat treatment of meibomian gland dysfunction is disclosed in European Patent Application serial no. PCT/GB2003/004782 titled "Eyelid Margin Wipes Comprising Chemical Means for Temperature Adjustment". As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without its drawbacks in that lid irritation can be exacerbated by non-specific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power. Goto, E., et al., Treatment of Non-Inflamed Obstructive Meibomian Gland dysfunction by an Infrared Warm Compression Device, British Journal of Ophthalmology, Vol. 86 (2002), pp. 1403-1407. This device is designed as a non-contact infrared heating mask using IR light emitting diodes. However, there are many potential problems with use of an IR heating mechanism. For example, the IR Heat can penetrate beyond the eyelid into the Cornia which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat. And furthermore, the device has no way of knowing how hot the tissue is getting. The temperature depends on blood flow rate in the eyelid as well as thickness which is different from patient to patient.

United States Patent Publication US2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects by Mitra et al, published in Eye, (2004) at pages 1-4. The problems associated with this invention are similar to those of the IR goggles in that no pressure or force is administered to the glands during heating.

United States Patent Publication US2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

SUMMARY OF CERTAIN EMBODIMENTS

In view of the above, a need for an imaging technique for imaging the eyelid, and particularly the meibomian glands of the eyelids is needed. It is therefore an object of embodiments consistent with the present invention to provide an imaging method and apparatus for imaging mammalian meibomian glands.

It is a further object of certain embodiments to provide high resolution images of the meibomian glands.

It is another object of certain embodiments to provide imaging techniques that produce images that can be stored and later retrieved or displayed.

It is still another embodiment of embodiments consistent with the present invention to provide a method of imaging meibomian glands that can be used to produce images that can be used to compare before and after treatment of the meibomian glands to determine a degree of effectiveness of treatment.

These and other objects and advantages will become evident upon review of the embodiments disclosed. It is noted that not all embodiments disclosed, taught or claimed herein necessarily meet each one of the objectives noted above, but that in no way should be construed to place the embodiment within or outside of the bounds of the inventions presented herein.

In one embodiment consistent with the present invention, a method of evaluating and treating dry eye in humans wherein the flow of naturally occurring secretion to the eye is reduced or stopped due to the presence of an obstruction of a meibomian gland in the eyelid involves imaging the glands to diagnose the condition of the meibomian gland; treating the meibomian gland to remove the obstruction from the gland; and re-imaging the gland to verify that the obstruction has been removed. The imaging can be carried out using at least one of VHF ultrasound imaging, OCT imaging, NIR optical imaging, infrared thermal imaging, trans-illumination photography, and visible light photographic imaging of the eyelid surface.

Many variations are possible. For example, in certain embodiments, an image resulting from the imaging can be processed by assignment of pseudocolors to the image. In certain embodiments, at least one of the imaging and the re-imaging is carried out with a force applied to the eyelid. In certain embodiments, the imaging is carried out using VHF ultrasound, and where the VHF frequency is between 80 and 160 MHz. In certain embodiments, the imaging is carried out using OCT imaging. In certain embodiments, the imaging is carried out using NIR optical imaging in the 0.650 to 2.5 micron wavelength In certain embodiments, the imaging is carried out using infrared thermal imaging in the 2.5 to 18 micron wavelength In certain embodiments, the imaging is carried out using visible light surface photographic imaging under magnification. In certain embodiments, the imaging is carried out using OCT imaging focused on a depth of 2 to 4 mm. In certain embodiments, the focus is fixed while in other embodiments, the focus is variable. In certain embodiments, the imaging is carried out using at least one of an A-scan, a B-scan and a C-scan. In certain embodiments, the imaging is carried out using trans-illumination photography. In certain embodiments, trans-illumination is produced by lighting the eyelid from the anterior surface thereof. In certain embodiments, trans-illumination is produced by lighting the eyelid from a posterior surface thereof. In certain embodiments, the imaging is carried out by scanning the surface that is trans-illuminated and processing resulting scanned images to produce a single image. In certain embodiments, at least one of the imaging and re-imaging is carried out while pressure is applied to the eyelid that simulates an amount of pressure caused by blinking the eyelid.

In certain embodiments, a method of evaluating dry eye in humans wherein the flow of naturally occurring secretion to the eye is reduced or stopped due to the presence of an obstruction of a meibomian gland in the eyelid involves applying a pressure to the eyelid that mimics pressure applied during blinking; and simultaneously imaging the glands to diagnose the condition of the meibomian gland. In certain embodiments, the method further involves treating the meibomian gland to remove the obstruction from the gland; and re-imaging the gland to verify that the obstruction has been removed. In certain embodiments, the imaging is carried out using at least one of VHF ultrasound imaging, OCT imaging, NIR optical imaging, infrared thermal imaging, trans-illumination photography, and visible light photographic imaging of the eyelid surface.

In another embodiment, a method of evaluating dry eye in humans wherein the flow of naturally occurring secretion to the eye is reduced or stopped due to the presence of an obstruction of a meibomian gland in the eyelid involves applying a pressure to the eyelid that mimics pressure applied during blinking; simultaneously imaging the glands to diagnose the condition of the meibomian gland; treating the meibomian gland to remove the obstruction from the gland; and re-imaging the gland to verify that the obstruction has been removed, wherein the imaging and re-imaging are carried out using an imaging process selected from the group consisting of VHF ultrasound imaging, OCT imaging, NIR optical imaging, infrared thermal imaging, trans-illumination photography, and visible light photographic imaging of the eyelid surface.

The above overviews are intended to illustrate exemplary embodiments which will be best understood in conjunction with the detailed description to follow, and are not intended to limit the scope or meaning of the appended claims.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which:

FIG. 4 is another cutaway view of meibomian gland 20 illustrating approximate positioning of the eyelid and the eyeball.

FIG. 5 is another cutaway view of meibomian gland 20 having a bulging plug in its orifice when pressure is applied that is imaged in a manner consistent with certain embodiments of the present invention.

FIG. 7 is a two dimensional depiction of an image of an eyelid having plugged meibomian glands prior to application of a pressure suitable for causing physical deformities at or about the orifice of the meibomian gland in a manner consistent with certain embodiments of the present invention.

FIG. 8 is a two dimensional depiction of an image of an eyelid with plugged meibomian glands with a pressure applied to cause physical deformities at or about the orifice in manner consistent with certain embodiments of the present invention.

FIG. 9 is a two dimensional depiction of an image of the eyelid of FIG. 8 after treatment to unplug the meibomian glands with pressure again applied to cause any remaining orifice obstructions to become observable in a manner consistent with certain embodiments of the present invention.

FIG. 10 is an example of a visualization system consistent with certain embodiments of the present invention.

FIG. 13 is a perspective view of a first embodiment of the meibomian gland evaluation tool according to the present invention.

FIG. 14 is a broken away side view of an embodiment of the meibomian gland evaluation tool according to the present invention.

DETAILED DESCRIPTION

Figure 1:
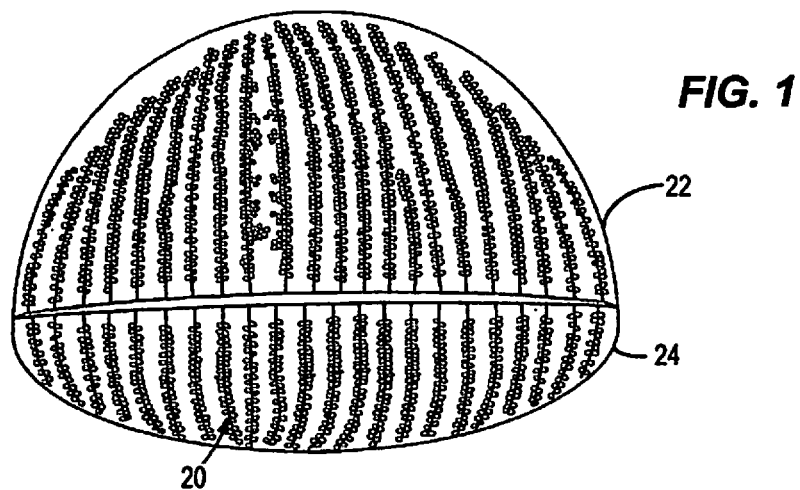
FIG. 1 depicts upper and lower human eyelids showing the meibomian glands.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The term "program" or "computer program" or similar terms, as used herein, is defined as a sequence of instructions designed for execution on a computer system. A "program", or "computer program", may include a subroutine, a function, a procedure, an object method, an object implementation, in an executable application, an applet, a servlet, a source code, an object code, a shared library/dynamic load library and/or other sequence of instructions designed for execution on a computer system, and may be stored in a form of software or firmware.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

As noted above, dry eye states have many etiologies. A common cause of common dry eye states is the condition known as "meibomian gland dysfunction", a disorder where the glands are obstructed or occluded. As employed herein the terms "occluded" and "obstruction" as they relate to meibomian gland dysfunction are defined as partially or completely blocked or plugged meibomian glands having a solid, semisolid or thickened congealed secretion and/or plug of any composition, leading to a compromise, or more specifically, a decrease or cessation of secretion. Also with a reduced or limited secretion the meibomian gland may be compromised by the occluded or obstructive condition as evidenced by a yellowish color indicating a possible infective state, or may be otherwise compromised so that the resulting protective lipid protective film is not adequate.

Imaging of the meibomian glands of the human eyelid as well as imaging while simultaneously applying pressure to mimic the normal expression of secretion from the meibomian glands by blinking enables study of the dynamic function of the meibomian glands and resulting pathology. The imaging of the meibomian glands while simultaneously applying pressure permits the viewing of the anatomical features of the gland with and without pressure and the observation of the effects of the pressure on the movement of the secretory material within and out of the gland. The latter observations permit the diagnosis of gland dysfunction and obstruction and the specific diagnosis of the site of the pathology within the gland or over the gland orifice.

As noted earlier, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells manufacture the secretions of the meibomian gland. The secretions flow from each acinus to the duct. While currently it has not been established with certainty, there appears to be a valve system between each acinus and the central duct to retain the secretion until it is required, at which time it is discharged in to the central duct. The meibomian secretion is then stored in the central duct and is released through an orifice of each gland onto the surface of the eyelid at the eyelid margin. The central duct leading to the orifice is on the order of 100 microns or less in diameter. Blinking and the squeezing action of the muscle of Riolan surrounding the meibomian glands are currently believed to be the primary mechanism to open the orifice for the release of secretion from the meibomian gland.

There is currently no truly acceptable method of imaging the meibomian gland and related structures of the eyelid in order to evaluate the function of the glands. Moreover, there is currently no truly acceptable mechanism to evaluate the dynamic function and resulting pathology of the meibomian gland.

In order to better understand the dynamic function and resulting pathology of the meibomian glands, certain embodiments consistent with the present invention utilize the application of varying levels of pressure to the glands in order to observe the gland when a pressure comparable to that exerted by the blink is applied over the meibomian glands. The pressures of the lids during normal blinking are minimal—perhaps on the order of only several grams per square mm of pressure. Many individuals with dry eye conditions practice forced blinking where the lids are squeezed together tightly with maximum pressure as an aid in expression of the meibomian secretion which are not adequately expressed with normal blinking due to partial meibomian gland obstruction. It should also be noted that there may be a wide variance in the efficacy of the approximately 50 meibomian glands of both eyelids, where some glands will be totally obstructed, some partially obstructed with minimal secretion, and some with varying degrees of normal secretion.

The application of a pressure of varying degrees the external surface of the eyelids while simultaneously imaging the meibomian glands allows the visualization of the dynamic status of the gland relative to the following:

Whether the secretory material with the application of a pressure to the external lid flows from the acini to the central duct or the secretory material is trapped and stagnated within the acini. One cause for this that has been advanced in the literature is an obstruction in valves that may be present in the acini at their junction to the central duct. Heretofore, this observation and diagnosis has never been reported. It may also be possible to observe the anatomical features which regulate flow from the acini into the central duct and their actions observed under application of varying pressures leading to a diagnosis that will facilitate treatment methods.

The central duct should be open without obstruction or adhesions and contain the liquid contents of the secretions from the acini. Imaging and observation will identify the nature and the location of any obstruction or adhesion. The diagnosis of the status of the central duct has never been reported (other than with biopsy specimens). Imaging of the central duct will facilitate development and utilization of treatment methods.

The central duct should discharge the secretory contents through the orifice onto the lid margin and to the tear film with the application of a pressure to the external lid mimicking the pressures of a blink. The discharge occurs through the orifices of the meibomian glands, which are situated in the lid margin and are closed unless a pressure is applied either through blinking or by manual means. Imaging of the gland simultaneously with the application of pressure will reveal the flow characteristics within the gland and the nature of the flow through the central duct and the terminal duct ending at the orifice.

If the application of a pressure to the external lid does not result in the expression of secretion from the gland, appropriate imaging will reveal whether the application of the pressure results in a pouting, bulging or a change in shape of the orifice. When the secretory material is compressed into the orifice, if there is overgrowth of tissue over the gland orifice, there will be pouting or other physical deformation of the contents at the end of the orifice, the pouting resulting from the overgrowth of epithelium over the gland which will extend with the pressure from the compression of the contents. This indicates that the obstruction is not primarily within the duct, but is the result of obstruction of the duct by the overgrowth of epithelium of the lid margin over the duct. Specific treatment to relieve the overgrowth is therefore indicated. If on the other hand there is no pouting of the gland or other physical deformation at the orifice surface, the obstruction would more likely be internal, and the location of such obstruction would advantageously be shown by certain of the imaging techniques consistent with certain embodiments of the present invention (or could at least be deduced by a lack of observable pouting or other deformities of the orifice). Treatment could then therefore be directed to the internal cause.

Application of pressure also may result in secretion of materials whose color, consistency and other characteristics can facilitate diagnosis.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland and compromise the secretory functions of the individual meibomian glands. More particularly, these keratotic obstructions can comprise combination of bacteria, sebaceous ground substance, dead, and/or desquamated epithelial cells. While meibomitis is obvious by inspection of the external lids, meibomian gland dysfunction may not be obvious even when examined with the magnification of the slit-lamp biomicroscope, since there may not be external signs or the external signs may be so minimal that they are overlooked. The external signs of meibomian gland dysfunction may be limited to subtle alterations of the meibomian gland orifices, overgrowth of epithelium over the orifices, and pouting of the orifices of the glands with congealed material acting as obstructions, for example.

In view of the difficulty of diagnosis of the function of the meibomian glands by simple magnified visual inspection, and the lack of existing criteria for evaluation of the degree of dysfunction of the meibomian glands, the inventors have determined that there is a need for imaging techniques that can be employed in the diagnostic processes. While imaging of various portions of the human anatomy have been studied and developed extensively, techniques for suitable imaging the meibomian glands, other than magnified visual examination, are non-existent. Imaging of the meibomian glands present unusual and specific problems in imaging.

Several different mechanisms can be provided for imaging the eyelid to provide imaging to assist in diagnostic as well as pre and post treatment evaluation of the proper function of the meibomian glands of the eyelid. While the human eye is of greatest interest, the techniques described herein may also be applied to other mammalian eyelids as well as other similar glands, with human eyes being referenced by way of example herein.

The typical human eyelid is less than 5 mm in thickness, and is most often less than about 4 mm in thickness. An eyelid that is 5 mm or more in thickness constitutes a quite thick eyelid for a human subject. The upper eyelid contains approximately 25-30 meibomian glands while the lower eyelid contains approximately 20-25 meibomian glands. In most instances, the meibomian glands are situated within the eyelid approximately ⅔ of the way from the front to the rear of the eyelid. The central tube of a small sample of glands that have been measured are roughly 100 microns in diameter (with a great deal of variation anticipated since only a limited number of glands have actually been measured at this writing). Also to identify a full or partial meibomian gland obstruction, either fully or partially, the imaging should preferably have a resolution down to approximately 1 to 10 microns with 1 to 5 being desired. This presents a rather unusual imaging problem in that the gland is quite small, is situated on a curved surface, is located at a very sensitive part of the body and requires rather high resolution imaging to actually observe. Hence, one or more techniques that can be used with relative comfort to the patient and which result in resolution that is high enough to be of value to the clinician are needed. Imaging these glands is further complicated by the relatively small size of the glands and lack of clear reference points to identify one particular gland and distinguish it from other glands. Currently, no numbering or other identification system to isolate a single gland exists, partially due to the variation in number of such glands, and difficulty in establishing standards in the absence of satisfactory imaging.

As noted, these glands can become clogged to produce varying degrees of "dry eye syndrome". Normally, the meibomian glands produce clear oil which, together with tears, serves to keep the eye lubricated and cleansed. However, meibomian glands can become clogged for a variety of reasons (many even potentially unknown). In such circumstances, the secretion of natural oils is inhibited or stopped altogether. The obstructive materials or plugs that occlude the glands when examined after their expression from the gland take on various physical appearances including, but not limited to, clear gel, a petroleum jelly like appearance, milky colored or hard white wire-like appearance. Also the physical appearance can be oil; inspissated jelly like; globular or bead like; filamentary from thin wire like to thicker filaments resembling tooth paste expressed from the tube. The color can be clear, tinged off white varying to yellow indicating infection and pus. Each such clog reduces the amount of oil available from a clogged gland to lubricate the eye, leading to inflammation and/or discomfort.

In most instances the lower eyelids are of most interest since they appear to generally be a primary source of secretion of the natural oils, and are most frequently the culprit when a patient presents with dry eye syndrome related to occluded meibomian glands. The upper eyelids tend to be less problematic—perhaps due to gravity assisting in the flow of lipids therefrom.

Current diagnosis techniques are limited to microscopic visual inspection of the top of the glands at the lid margin. There is no known technique that can provide imaging that can provide before and after images in order to assess the success of any given treatment. The lack of a consistent diagnosis tool to obtain before and after comparison images of the operation of the glands and treatment success further leads to problems in insurance reimbursement for the physician.

Several variations of visualization of the meibomian glands are presented herein. It will be understood that many variations of the embodiments taught will be evident to those skilled in the art upon consideration of the present teachings. Each of the technologies described herein can be implemented using either stationary apparatus into which the patient places his or her eye during imaging (e.g., with stabilization of the patient's head by chin and forehead rests), and handheld apparatus which is placed in appropriate proximity to the eyelid by the physician or technician during testing.

Figure 2:
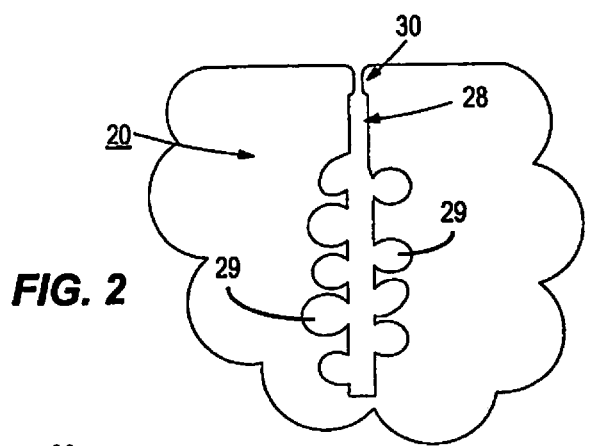
FIG. 2 is a cutaway view of an illustrative meibomian gland 20.

Referring now to FIG. 1, the location of the meibomian glands 20 are shown on the upper and lower eyelids 22 and 24 respectively. As briefly stated herein above, the upper lid contains about 25 meibomian glands and the lower lid contains about 20 meibomian glands, with significant variation. As shown in cross-sectional view of one gland 20 in FIG. 2, each gland includes a central duct or channel 28 into which the secretion flows from acini 29 and an orifice 30 which opens on to the eyelid margin and through which the secretion flows in order to be added to the tear film upon blinking. It will be seen that the glands are of different size, depending upon the location in the eyelid and that the orifice 30 is narrower than the central duct 28.

Figure 3:
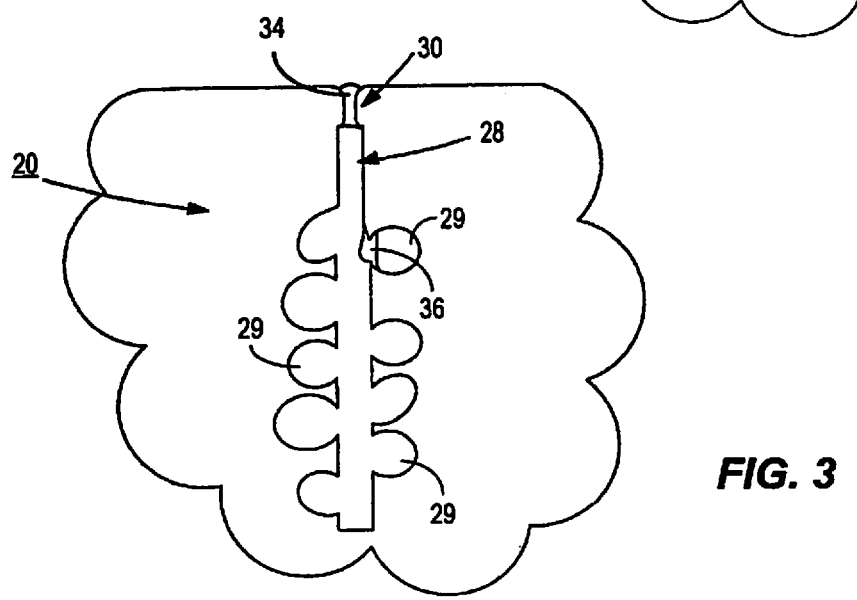
FIG. 3 is a cutaway view of meibomian gland 20 illustrating a plugged orifice.

Obstruction composition will vary with the etiology which produced it. However, the obstruction will, in most cases observed to the present, be a combination of, dead cells, bacteria, desquamated cells, desquamated cells aggregating in keratotic clusters, milky fluid, inspissated or creamy secretions, or any combination of the foregoing in solid, semi-solid and thickened forms. Referring to FIG. 3, a simplified view of exemplary obstructions to gland 20 is depicted. In this example, which is by no means necessarily representative of all meibomian gland obstructions, as explained above, a solid or semi-solid or thickened plug 34 is depicted which is fully occluding the orifice 30 of gland 20. Another obstruction 36 is shown at a junction from one of the acini with the central duct. As previously noted, this may be the site of a valve in the gland structure, but embodiments consistent with the present invention should not be limited by theories of the actual meibomian gland structure.

Surface Imaging

One mechanism for providing imaging of meibomian glands for both diagnosis and post treatment evaluation is depicted in FIGS. 4-9. FIG. 4 depicts a cutaway view of meibomian gland 20 illustrating approximate positioning of the lower eyelid 24 and the eyeball 42. Details such as the eyelashes have been omitted for illustrative clarity. In some instances, microscopic observation can detect the presence of a plug 34 in meibomian gland 20, or adjacent meibomian glands. However, in many instances, simple visual observation is inadequate to clearly document and specifically identify the location or locations of an occluded meibomian gland 20, particularly depending upon the nature of the plug 34. It is also noted that magnification levels of 25× to 50× at least are advantageous in observation of the orifice at the surface of a meibomian gland. However, such high magnification is difficult to use due to the great exaggeration of even very small movements of the patient.

However, plugged glands such as gland 20 can be more readily identified using the technique illustrated in FIG. 5, which depicts another cutaway view of meibomian gland 20 having a bulging plug 34 or puckering or other physical deformation at the orifice 30 in its orifice that is imaged in a manner consistent with certain embodiments of the present invention. In this embodiment, a tool 46 (which may simply be a finger, but is preferably a calibrated instrument as will be described later) is pressed against lower eyelid 24 in a controlled manner, while the upper eyelid is held open, with the pressure illustrated by arrow 50. This pressure compresses the eyelid from the anterior surface, and thus the meibomian gland 20 so that fluid present inside the gland 20, exerts upward pressure on the plug 34 to produce a bulge, pucker or other physical deformation at the surface of the eyelid at or about the location of the orifice as illustrated.

Images can be made using a camera 54 with suitable magnification (depicted as 58), e.g., attached to an ophthalmologic microscope or bellows and/or macro focus lens of suitable focal length, lighting and magnification to image a desired region of the eyelid and freeze or minimize the effects of patient movement. Flash photography or high light-high shutter speed photography can be used to freeze motion if needed. In other embodiments, pressure can be exerted from either or both the anterior and posterior surfaces of the eyelid to thereby squeeze the meibomian glands. The application of pressure on the eyelid and imaging of the secretion is also useful in diagnosis. Depending on the color, consistency and presence of the secretion one can categorize the amount of meibomian gland dysfunction (MGD). The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained. As noted above, obstruction composition will vary with the etiology which produced it. However, the obstruction will, in most cases observed to the present, be a combination of, dead cells, bacteria, desquamated cells, desquamated cells aggregating in keratotic clusters, milky fluid, inspissated or creamy secretions, or any combination of the foregoing in solid, semi-solid and thickened forms.

A similar procedure can be carried out for imaging the upper eyelid, however it is believed at present that approximately 70% of dry eye problems are associated with meibomian gland dysfunction with the lower eyelid. Accordingly, diagnosis and treatment of the lower eyelid may be of most significance in many cases. However, this is not intended to preclude imaging of the upper or both eyelids.

Figure 6:
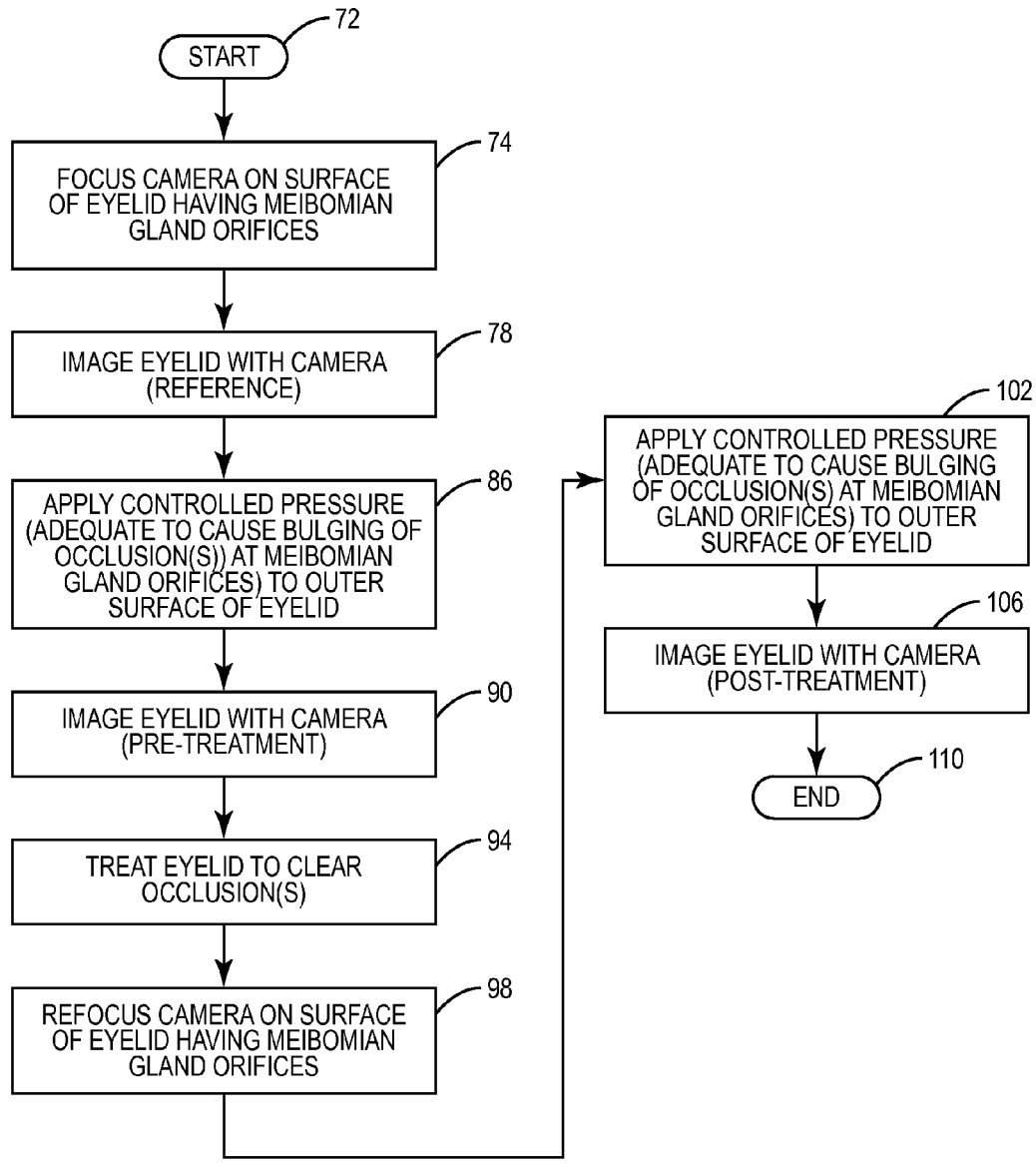
FIG. 6 is a flow chart of an exemplary orifice surface imaging process consistent with certain embodiments of the present invention.

FIG. 6 is a flow chart of an exemplary orifice surface imaging process 68 consistent with certain embodiments of the present invention starting at 72. Many variations of this process are possible depending upon what images are desired for a particular purpose. At 74, camera 54 is focused on the eyelid surface carrying the meibomian glands (in this example, the upper surface of the lower eyelid 24 at an angle suitable to produce perspective of the raised bulge or pucker or other physical deformation 34 at the surface). If desired, at 78 an image can be generated at this stage to document the normal state of the glands. Certain of the glands may appear clearly occluded in this image, but the image may not reveal all occlusions (e.g., 36).

FIG. 7 is a two dimensional depiction of an image of the eyelid having plugged meibomian glands at this stage of the process and prior to application of a pressure suitable for causing the plugs of the meibomian glands to bulge or the orifice to pucker or produce other observable physical changes in a manner consistent with certain embodiments of the present invention. For ease of illustration, the image is depicted as being taken from approximately normal to the outer surface of the eyelid, rather than at an angle showing perspective of the surface containing the orifice. Any variety of angles can be used for the images depending upon the patient, diagnostician preferences, etc. This image, if desired and taken, can be used for reference and for detection of obvious occlusions which show up as visible bulges or puckers representing a plug which may produce a recognizable pattern and colorations for comparison when a post treatment image is taken. This image can also be compared with the image of FIG. 8 as will be described later, to determine the presence of occlusions that would not be visible without application of pressure to create bulges or puckers 84 (an analogous physical deformation at the surface wherein the tissue surrounding a plugged orifice bulges around the plug to create a "pucker" effect) as illustrated.

Referring back to FIG. 6, at 86, a controlled pressure is applied to cause bulging or puckering or other physical deformation of occluded meibomian gland orifices. This pressure can be applied in a number of ways as will be described later, but are generally in the range of pressures that would simulate or mimic a patient blinking his eyes. Once the bulges or other physical deformations are apparent, at 90 they may be imaged using camera 54 to produce, for example, an image as depicted in FIG. 8 which shows a two dimensional depiction of an image of an eyelid with plugged meibomian glands with a pressure applied to cause the plug 34 to bulge or pucker to produce the physical deformations illustrated as 84 in FIG. 8 in a manner consistent with certain embodiments of the present invention. The images of FIGS. 7-8 can be used to gauge the degree, location and number of observable dysfunctional meibomian glands and to create a record thereof. Analogous records are often necessary to assure insurance reimbursement and to establish nature and degree of occlusion of the meibomian glands for diagnostic purposes.

Referring back to FIG. 6, a treatment can be conducted, as at 94, the success of the treatment can also be gauged using post treatment imaging. Thus, at 98, the camera can be refocused on the same eyelid and the controlled pressure again applied at 102 to induce bulging or puckering or other surface deformations at the orifice of occluded meibomian glands. A post treatment image can then be made at 106 with this exemplary process ending at 110.

FIG. 9 is a two dimensional depiction of an image of the eyelid of FIG. 8 after treatment to unplug the meibomian glands with pressure again applied as in 102 to cause any remaining obstructions to cause bulges or puckers 84 (two depicted) in a manner consistent with certain embodiments of the present invention.

While the above description may imply the use of still images, moving images can also be utilized, for example, to produce a pan across the eyelid at a microscopic level to image the entire eyelid. Alternatively, a suitably wide angle image with high enough visual resolution can be captured to provide ease of reference for relocation of clogged glands. The diagnostician may also apply markings to the eyelids to serve as reference points in the images to more readily identify a particular gland.

In order to assure clarity of the microscopic images, the image should preferably be produced under circumstances wherein the object being imaged is as stable as possible with exposure times being minimized. In this case, the head can be stabilized in a conventional manner using conventional ophthalmologic chin and forehead braces as are used in conventional ophthalmologic exams, with the examination braces fitted with suitable visual light photography instruments as described herein.

FIG. 10 depicts a more detailed setup for visible light imaging according to certain embodiments in which camera 54 is used, through suitable magnification represented by 58, to capture an image of the eyelid (e.g., lower eyelid 24) and associated meibomian gland 20. Images from camera 54 may be rendered using either conventional photographic processes or can be directed to an image processing computer 208 that can then process and possibly enhance the image, for example by shifting of brightness, color, gamma function, sharpness or contrast. The image can then be displayed on a display monitor 212, and/or stored on disk or other storage 210, or printed on a photographic quality printer 216 or any or all of the above. In addition to still images, moving images can similarly be captured in this manner to produce, for example, a pan across the eyelid in which individual frames can be captured and printed if desired. Due to the high magnification, a step and repeat process that captures a portion of the eyelid and then steps across can be used, with focusing being carried out as the camera is swept about an arc to remain normal to a selected profile of surface being imaged.

In certain embodiments, as further depicted in FIG. 10, a camera 54 and possibly light source(s) (not shown) can be moved across the eyelid in an organized manner (i.e., in a suitable arc) using an X-Y or X-Y-Z controller 220 and a suitable servo motor arrangement 222 under control of a programmed processor such as computer 208 in order to scan the entire eyelid. Scanning the eyelid can thus be accomplished manually or by use of an X-Y-Z control system. Similarly, the application of pressure to the eyelid can be effected either manually, with manual control determining when to create the image, or by coordinated action of a pressure applying probe also operating under control of the computer 208 via servo control. In other embodiments, a single probe device can apply pressure to the entire eyelid as the camera 54 is manipulated manually or by step and repeat actions under control of the computer 208 in conjunction with controller 220 and servos 222. Many variations are possible without departing from embodiments consistent with the present invention.

In order to provide references for identification of the meibomian glands, a reference scale or markings can be imaged along with the surface in order to be able to later identify the location of particular glands.

Figure 11:
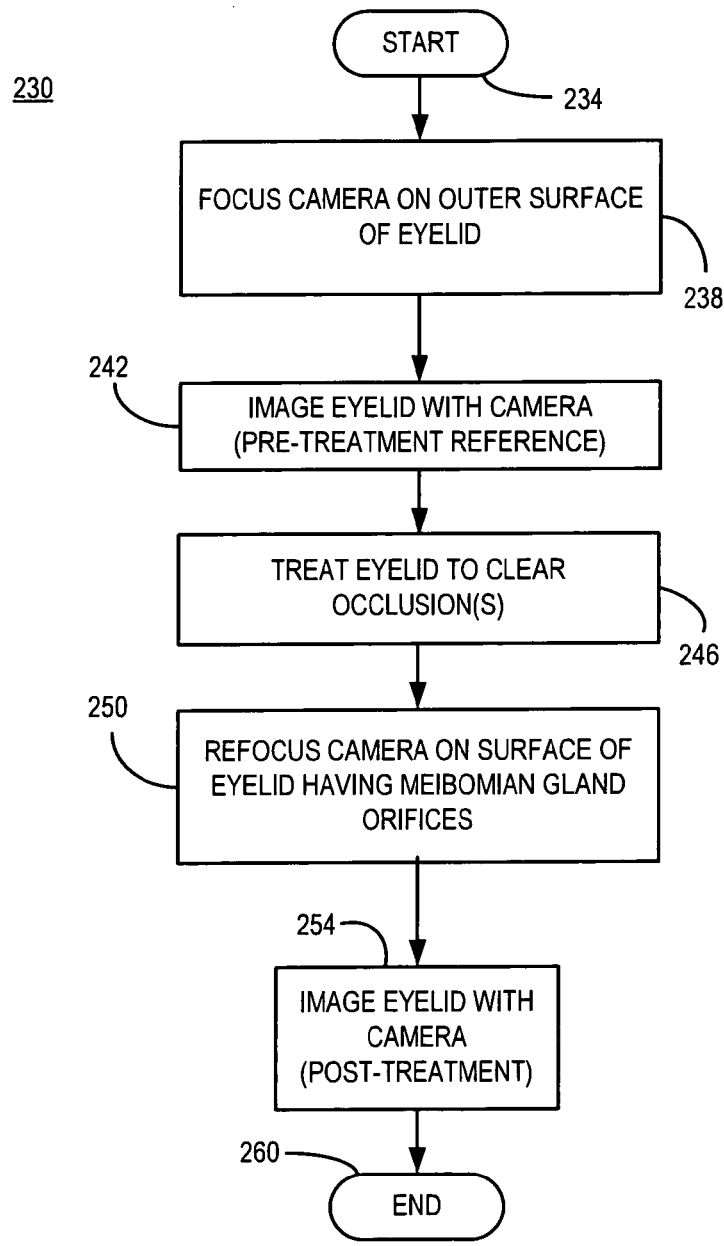
FIG. 11 is an example of a method consistent with certain embodiments of the present invention.

FIG. 11 depicts an exemplary process 230 for imaging the meibomian glands in a manner consistent with certain embodiments of the present invention starting at 234 after which the camera 200 is focused on the surface of the eyelid. One or more images are then created at 242 to create a pretreatment reference image. This image may be processed as described above, either by fully automated means of with the assistance of manual intervention to highlight significant attributes by color modification or enhancement. The glands may then be treated using any suitable treatment mechanism at 246. The effectiveness of the treatment can then be evaluated by imaging the eyelid in the same manner as previously by refocusing the camera on the eyelid at 250 and re-imaging the eyelid and enhancing as needed at 254. The process ends at 260. A similar process can be used with any of the imaging techniques discussed herein.

Figure 12:
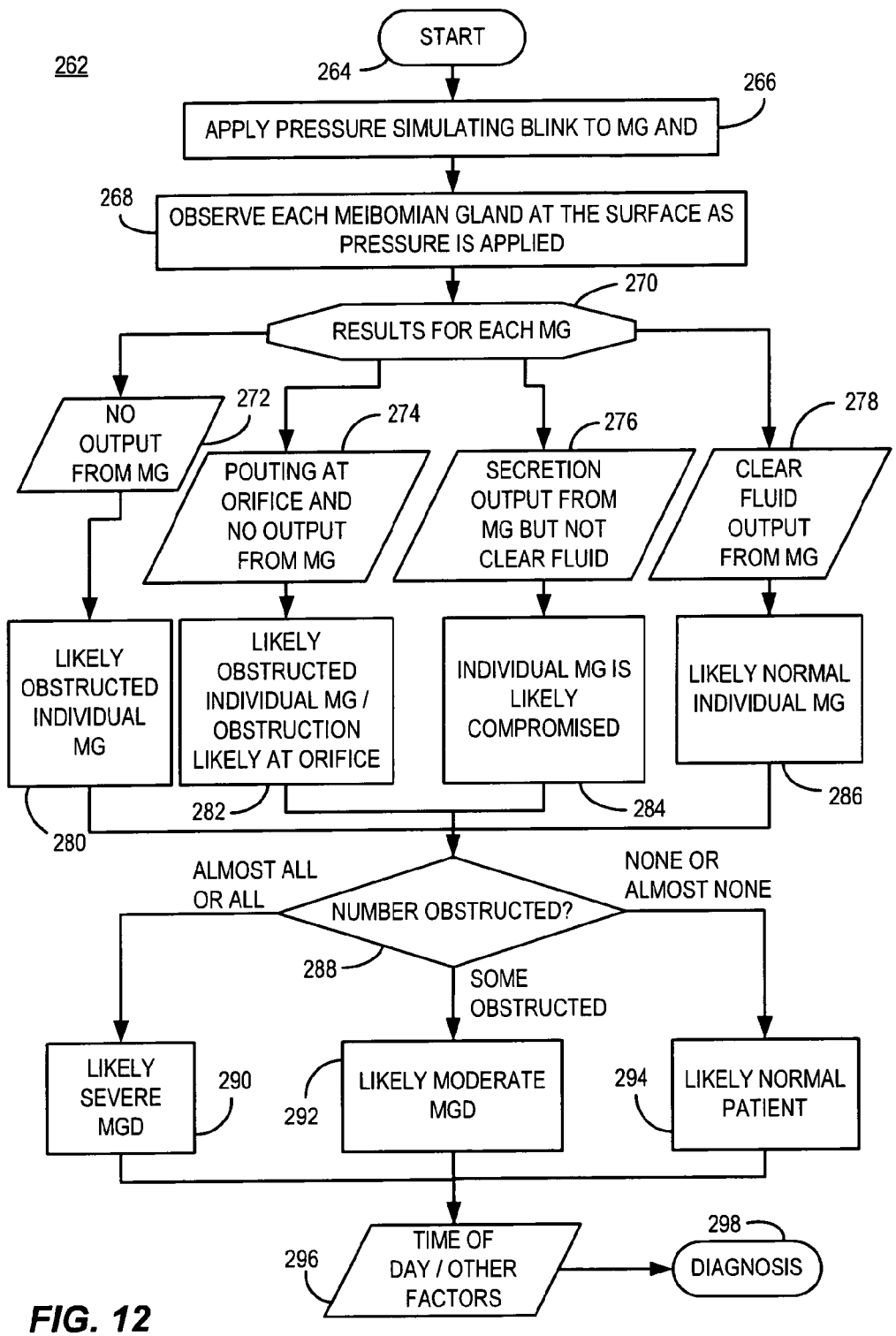
FIG. 12 is an example of a diagnosis tree consistent with certain embodiments of the present invention.

Diagnosis of the condition can be made with a reasonable degree of accuracy using the present methods in conjunction with a decision system such as the flow chart depiction of a decision tree 262 of FIG. 12 starting at 264. At 266 where the physician or technician applies pressure to the eyelid adequate to mimic the pressure applied when a person blinks. At 268, each meibomian gland is observed at the surface as the pressure is applied for results at 270. Any of several results can be observed as follows. No output from the individual MG at 272, no output from the individual MG accompanied by pouting or other physical deformation at the orifice when pressure is applied at 274, secretion output from the MG—but the secretion is not clear fluid at 276, or clear fluid output is secreted by the MG at 278.

When there is no output from the individual MG at 272, it can be tentatively concluded that the individual MG is likely obstructed at 280. When there is pouting or other physical deformity at the orifice, it can be concluded that the MG is likely obstructed and it is further likely that the obstruction is at or near the orifice at 282. If the individual MG secretes output, but it is not a clear fluid, at 276, it can be concluded at 284 that the individual MG is likely compromised (e.g., by obstruction, inflammation, infection, etc.). When clear fluid is output from the MG at 278, the individual MG is likely to be functioning normally or nearly normally at 286.

Since this assessment is made on a gland by gland basis, it is difficult for a doctor or technician to make the assessment while continually moving and refocusing his microscope, and moving the probe used to simulate the blinking pressure. Also, since the probe may repeatedly stimulate secretion from adjacent glands, it is possible to reduce or deplete the available fluids from one or more glands, skewing the test results. Hence, it is advantageous for the surface to be imaged during this process so that the assessment can be made on multiple glands with a single application of pressure and so that a reliable accounting for all or most glands can be made. This is extremely difficult to effect accurately without imaging of the surface.

Once all of the glands have been imaged and the results evaluated for each gland, an overall assessment can be made at 288. If almost all or all glands are obstructed at 288, it is likely that the patient has severe MGD at 290. If a moderate number of the glands are obstructed at 288, the likelihood is that the patient has moderate MGD at 292. If none of the glands are obstructed or only a few are obstructed, the patient likely has normal meibomian gland function at 294. The greater the number of obstructed or compromised meibomian glands, the more severe the MGD. It is difficult or impossible to provide an accurate absolute number of normally functioning glands that constitute normal MG function, since the number of glands per patient varies, as does the glandular output. Thus, some level of experience and judgment should be factored into the ultimate diagnosis. However, if all, or the great majority yield clear oil, there is probably no MGD.

At 296, other factors should be taken into consideration in making a final determination as to the presence of MGD and its severity at 298. For example, it is possible for a gland to be normal, but all of the secretion has been previously secreted during the day. In this case, the evaluation might not show any secretion upon the application of the pressure, but the gland would still be normal if it were evaluated early in the day before all of the secretion had been used. This may happen with a few or with all of the glands at any given time. The later in the day or evening the greater the probability of this phenomenon, since the gland is believed to refill during sleep when there is no blinking and no normal secretion from the gland during sleep. Other factors that may be considered are the age of the patient, observable inflammation of growth over the orifice, history, hormonal conditions, etc.

Referring now to FIGS. 13 and 14 in which a first embodiment of a device for simulating blinking pressure on the eyelid is shown, the meibomian gland evaluation apparatus generally indicated at 300 comprises an elongate shaft or handle 305 having a bore 310 there through. Located at one end of handle 305 is an annulus 312 the purpose of which will become evident as the description proceeds. One end of handle 305 mounts a cap 315 having a bore there through 317 and the opposite end of handle 305 mounts a second end cap 320. The caps may be threaded, press fitted or otherwise connected, depending upon the particular fabrication technique and materials employed. For purposes of illustration only, cap 315 is press fitted and cap 320 is threaded.

Figure 15:
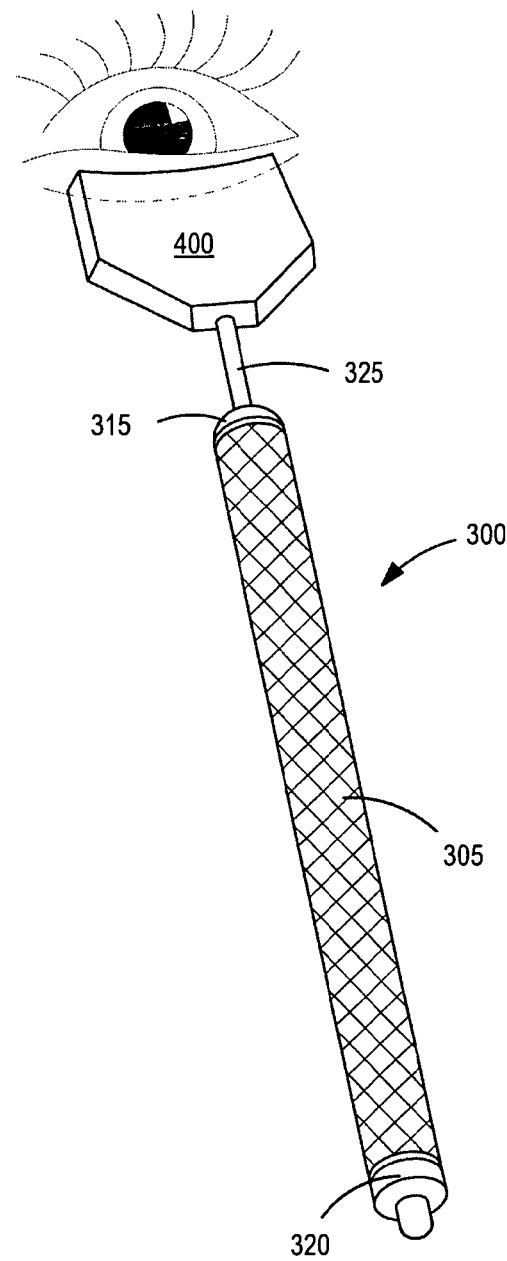
FIG. 15 is a perspective view of another embodiment of the meibomian gland evaluation tool according to the present invention.

A probe tip 400 is mounted on shaft 325 for longitudinal movement relative to the handle 305 such that when the probe tip 400 is placed against the eyelid and compressive force is applied, movement of the handle 305 a preselected distance replicates the approximate force required for natural expression of secretion from the meibomian gland. Testing has determined that this force is approximately 15 grams per 30 mm$^2$ however; depending upon the age, gender, race or other factors, this force may vary somewhat and be between approximately 10 grams per 30 mm$^2$ and 20 grams per 30 mm$^2$. Probe tip 400 is detachably connected to one end of a shaft 325 which is operatively associated with handle 305. Probe tip 400 is fabricated from a soft biocompatible material such as natural or synthetic rubber, Polyester® or other inert/non-allergenic or biocompatible materials, well known to those skilled in the art. As shown in FIG. 13, probe tip 400 is cylindrical and may be dimensioned to as to overlie one or more meibomian glands. An alternate embodiment of probe tip 400 is shown connected to the handle as illustrated in FIG. 15 and in that embodiment is designed to test a larger section of the eyelid to simultaneously evaluate multiple meibomian glands for gland function. Probe tip 400 may be press fit, snapped or threaded on to the end of shaft 325.

Per FIG. 14 shaft 325 also includes an annulus 312 proximate the tip mounting end. As shown, shaft 325 is inserted within bore 310 for longitudinal movement. A helical spring 335 is operatively associated with shaft 325 and surrounds a section thereof, biasing the shaft out of the housing. Annulus 312 serves as a support or bearing surface for spring 340.

Figures 16, 17:
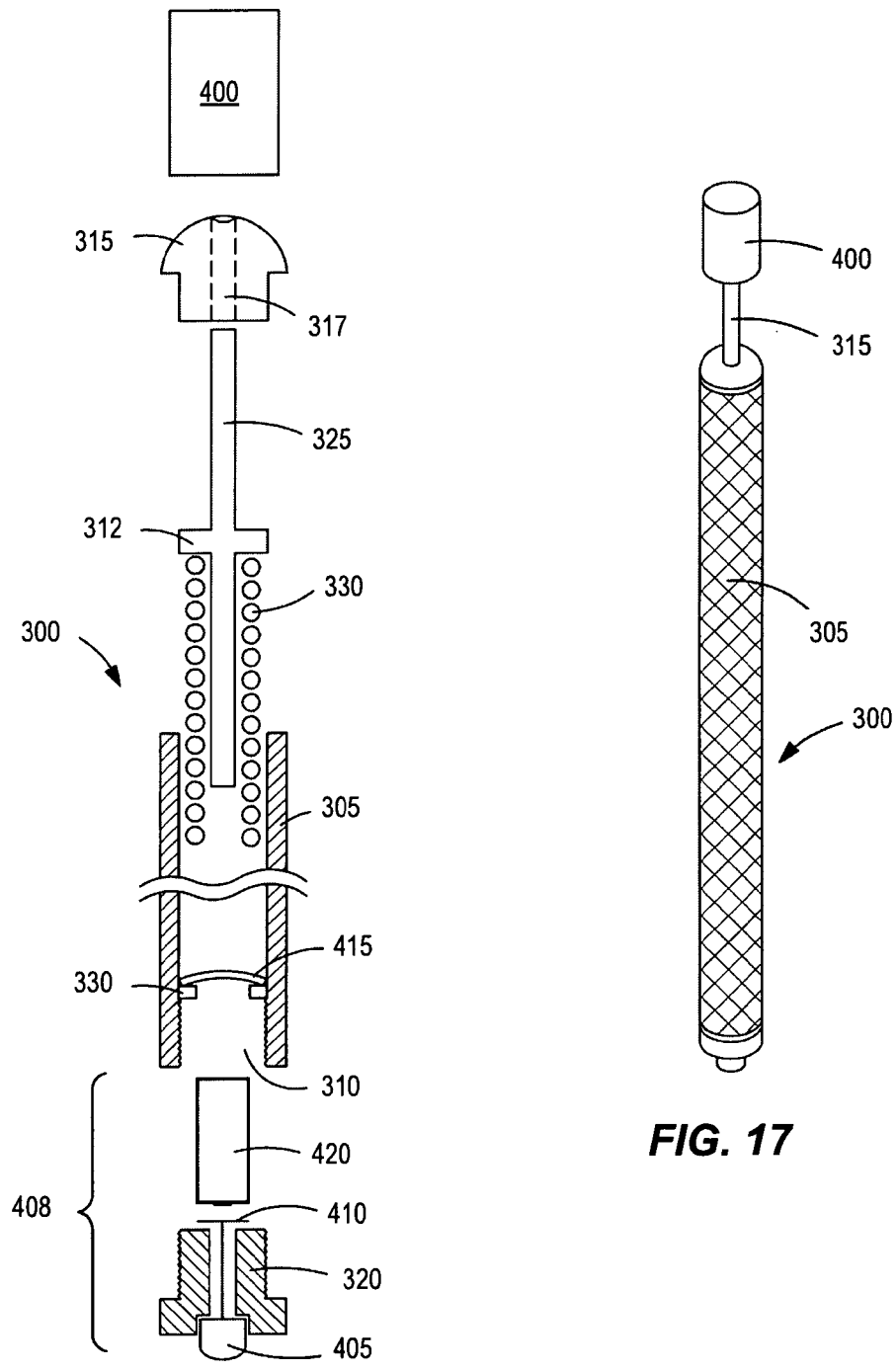
FIG. 16 a broken away side view of an embodiment of the meibomian gland evaluation tool according to the present invention.
FIG. 17 is another view of an embodiment of the meibomian gland evaluation tool according to the present invention.

As illustrated in the second embodiment of the invention, shown in FIGS. 16-17, the apparatus may also include an indicator means or indicator generally indicated at 408 for indicating when handle 305 has moved the preselected distance. The indicator means 408 may be selected from the group consisting of auditory, visual and tactile signals. Any of the just mentioned signal means may be employed so long as activation thereof does not significantly impact the force required to move the handle to ensure that the pressure delivered to the eyelid remains in the required range. The indicator means 408 comprises a visual indicator means or light emitting diode (LED) 405 mounted in end cap 320 such that the light emitting portion is at least partially external of the cap and the electrical leads 410 (schematically shown) extend down into the bore 310 and are connected to a battery contact plate 415 also within handle 305. A battery 420 is provided proximate the battery contact plate 415. The LED is activated by movement of the handle 305 which causes the end of shaft 325 to complete the electrical circuit and illuminate the LED. Movement of the handle 305 away from the eyelid opens the electrical circuit and turns off the LED. Circuits of this nature are well known the art and a detailed discussion thereof is not deemed necessary. Buzzers, vibrators or other indicator means may also be employed as visual indicator means.

Figure 18:
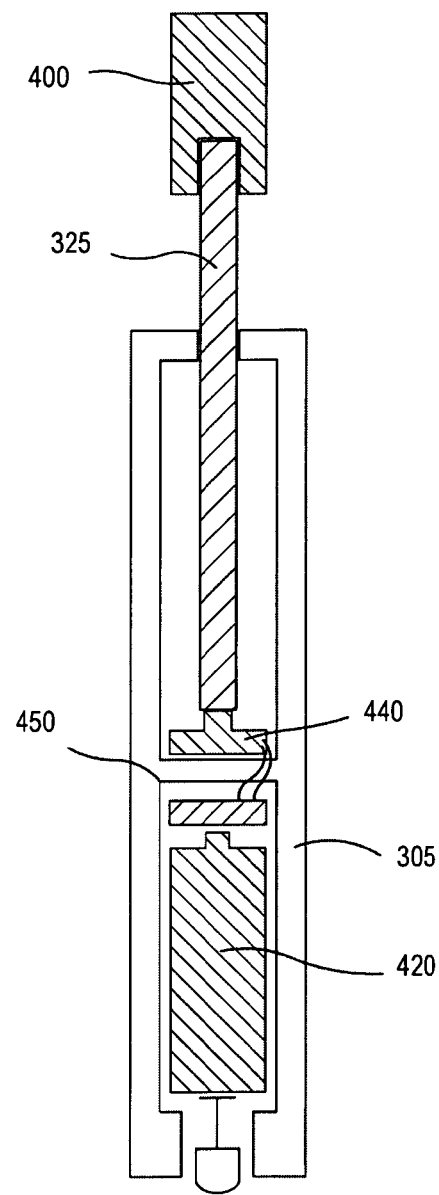
FIG. 18 is a cutaway side view of an embodiment of the meibomian gland evaluation tool according to the present invention.

In the embodiment of FIG. 18, the meibomian gland evaluation tool 300 is generally similar to the previously described embodiment except that the shaft 325 is substantially stationary and the means for sensing when the preselected pressure has been reached comprises a piezo-electric or other similar strain gauge device 440 in combination with an amplification circuit 450 (shown schematically) and which is well known to those skilled in the art. When the preselected pressure has been exerted on the eyelid, the amplifier is activated and the indicator means 408 is triggered. It is believed that this embodiment will be produced using molding techniques wherein the cylindrical handle 305 will be produced in two longitudinal halves and can be press fitted together.

Figure 19:
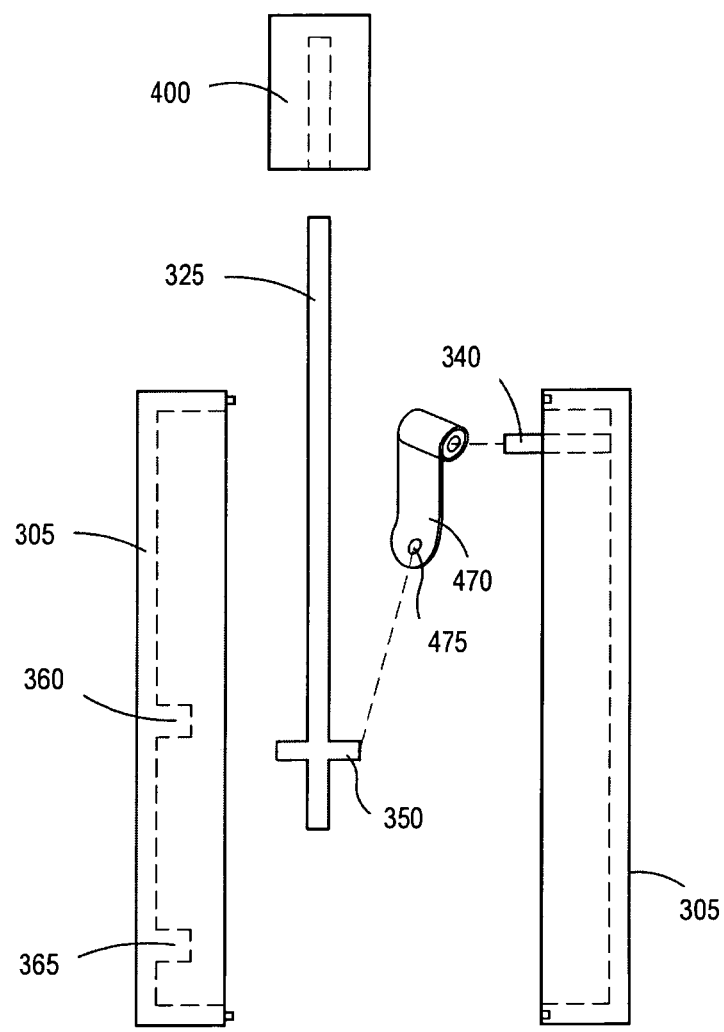
FIG. 19 is an exploded view of an embodiment of the meibomian gland evaluation tool consistent with embodiments of the present invention.

In the embodiment of FIG. 19, the preselected pressure is supplied by a spring means or constant force spring 470 which has a spring constant selected to deliver the preselected pressure to the eyelid. The constant force spring is coiled and has a connection opening 475 at the outer end. In this embodiment, it is again believed that the handle 305 will be molded in two opposing longitudinal sections that can be press fitted together. One half of handle 305 is provided with upper stop 360 and lower stop 365 in the form of protuberances extending into the bore 310 which operate to limit the travel of probe shaft 325, as will be described more fully herein below. In addition, one side of the handle includes a tang 345 extending from the inner handle wall towards the center of the bore 310. The tang 340 should be of a diameter to receive the opening in the center of constant force spring 470 and should be of a length sufficient to maintain the spring in place when the two halves of the handle are connected together. The other end of spring 470 is connected to a tang 350 located on shaft 325. In the "at rest" state of this embodiment, the spring 470 is in the coiled position and tang 350 is in contact with upper stop 360. Pressure exerted on the probe tip by movement of the handle 305 causes the spring to uncoil until tang 350 contacts lower stop 365. An indicator means is not provided as the constant force is delivered merely by unwinding spring 470. Further, it is believed that the clinician will sense when the shaft has reached its maximum path of travel when tang 350 contacts lower stop 365, but the indicator means which could buzz, flash, vibrate, or illuminate when shaft 325 is in the operating range between stops 360 and 365 could also be included with this embodiment of the invention.

Figure 20:
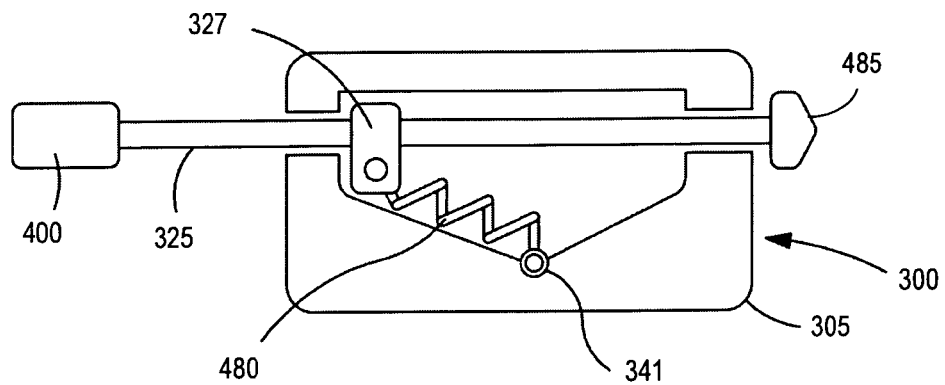
FIG. 20 is broken away side view of another embodiment of the meibomian gland evaluation tool according to the present invention.

FIG. 20 illustrates an alternate embodiment wherein the handle shape is rectangular and box-like. Shaft 325 includes a mounting bracket 327 to which one end of an over center spring or compression spring 480 is connected. As a compression spring is normally expanded, the first end rests in a cavity or pocket 341 in handle 305. The opposite end of spring 480 is connected to the bracket 327 by means of a pin or tang formed in the bracket and the shaft is biased in the extended or outward position. Pressure on the eyelid acts to compress the spring 470. When shaft 325 is pushed such that 327 is past the position of 341, shaft 325 will retract away from the eyelid. The device may be reset by pressing a reset button 485, as will be appreciated by those skilled in the art upon consideration of the present teachings.

Figure 21:
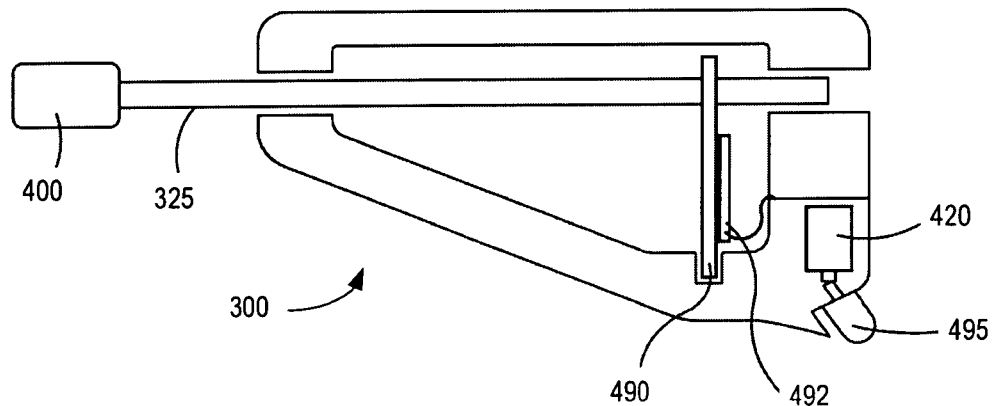
FIG. 21 is broken away side view of another embodiment of the meibomian gland evaluation tool according to the present invention.

FIG. 21 illustrates another embodiment of the meibomian gland evaluation tool 300 wherein the shaft 325 is connected to handle 305 with a cantilever beam 490. A piezo-electric transducer or strain gauge 492 together with actuator circuitry identical to that discussed in connection with the embodiment of FIG. 18. Pressure on probe tip 400 causes strain gauge to output a signal proportional to the applied pressure. When the preselected pressure has been reached, the actuator circuit activates LED 495.

In operation, considering for example the device of FIG. 16, the clinician selects the handle 300 having the desired probe tip 400 or mounts the desired probe tip 400 at the end of shaft 325. The probe tip 400 is then placed on the external surface of that section of the eyelid to be tested for meibomian gland function. The clinician also equips themselves with the proper equipment (appropriate magnification from a hand held lens, head magnifier, slit lamp, microscope etc.) to be able to observe the meibomian gland orifice(s). A compressive force in the form of gentle pressure is exerted upon the eyelid by pressing the handle 305 towards the eyelid which compresses spring 340. Just prior to the end of shaft 325 makes contact with the battery contact plate 415, the force of about 15 grams per 30 mm$^2$ is reached in a user independent manner and the clinician observes whether the meibomian gland is properly secreting or not. The apparatus is designed so that just prior to activation of the indicator means, the cumulative force or energy stored in the spring is substantially equivalent to the force required for natural meibomian gland secretion. Of course, the other indicator means are actuated in the aforementioned manner as well.

In another embodiment (not shown) of the meibomian gland evaluation tool 300, the shaft 325 may be connected to handle 305 which is attached to a coil spring of constant force which rotates and provides force either directly on the eyelid or by pushing a linear rod attached to the handle 305 which applies force on the eyelid.

It will be noted that this apparatus of the present invention may be fabricated as a disposable, single use item primarily from plastic materials, or alternatively, may be fabricated as a multiple use probe with disposable tips, in which case that portion of the device that is re-used will be fabricated from materials of sufficient durability to withstand repeated autoclaving. Many other variations of such a tool will occur to those skilled in the art upon consideration of the present teachings.

Thus, in one embodiment consistent with the present invention a method of imaging a mammalian meibomian gland of the eyelid involves focusing a camera on a surface of the eyelid containing an orifice of the meibomian gland; from the outer surface of the eyelid, applying adequate pressure to the eyelid to mimic the pressures applied to the meibomian gland during blinking of the eye, such pressure normally causing fluid within the meibomian gland to be expressed and to cause a fully occluded gland to exhibit physical deformities that are observable at the surface; and from the outer surface of the eyelid, capturing a diagnostic image of the surface of the eyelid.

In certain embodiments, the captured diagnostic image is stored in an electronic storage medium or displayed on a video display. In certain embodiments, the process further involves treating the occluded meibomian glands in an attempt to clear the occlusion; and repeating the focusing, applying pressure and capturing image to capture a post treatment image to thereby document a degree of success of the treating. In certain embodiments, the diagnostic image is compared with the post treatment image to determine a degree of effectiveness of the treatment. In certain embodiments, the pressure is applied using an instrument that applies a controlled amount of pressure in coordination with capturing the image. In certain embodiments, the pressure is between approximately 10 and 30 grams/30 mm$^2$. In certain embodiments, the pressure is applied using a hand-held instrument. In certain embodiments, the process further involves relating observable conditions in the image with symptoms of meibomian gland dysfunction to make a diagnosis. In certain embodiments, a proportion of meibomian glands that exhibit symptoms of compromised function to make a determination as to a severity of meibomian gland dysfunction. In certain embodiments, the proportion of meibomian glands that exhibit symptoms of compromised function comprise those meibomian glands that do not produce clear fluid. In certain embodiments, multiple images are taken of the eyelid in order to image multiple meibomian glands. In certain embodiments, multiple images are taken by a step and repeat action under automated control. In certain embodiments, a computer readable storage medium can store instructions which, when executed on a programmed processor, carry out any of the embodiments of the method.

In another embodiment, a method of diagnosing function of a human meibomian gland of the eyelid, involves providing a diagnosis decision tree; focusing a camera on a surface of the eyelid containing an orifice of the meibomian gland; from the outer surface of the eyelid, applying adequate pressure to the eyelid to mimic the pressures applied to the meibomian gland during blinking of the eye, such pressure normally causing fluid within the meibomian gland to be expressed and to cause an occluded gland to exhibit physical deformities that are observable at the surface; from the outer surface of the eyelid, capturing a diagnostic image of the surface of the eyelid; and relating observable conditions in the image with symptoms of meibomian gland dysfunction to make the diagnosis. In certain embodiments, the relating involves determining a proportion of meibomian glands that exhibit symptoms of compromised function to make a determination as to a severity of meibomian gland dysfunction. In certain embodiments, the proportion of meibomian glands that exhibit symptoms of compromised function comprise those meibomian glands that do not produce clear fluid. In certain embodiments, the proportion of glands that exhibit symptoms of compromised function comprise glands that secrete fluid that is not clear. In certain embodiments, the proportion of glands that exhibit symptoms of compromised function comprise glands that secrete no fluid. In certain embodiments, the proportions of glands that exhibit symptoms of compromised function comprise glands that secrete no fluid and exhibit physical deformation at the meibomian gland orifice. In certain embodiments, the captured diagnostic image can be stored in an electronic storage medium or displayed or rendered on a display or printed. In certain embodiments, the process further involves treating the occluded meibomian glands in an attempt to clear the occlusion; and repeating the focusing, applying pressure and capturing to capture a post treatment image to thereby document a degree of success of the treating. In certain embodiments, the pressure is applied using an instrument that applies a controlled amount of pressure in coordination with capturing the image. In certain embodiments, the pressure is applied using a hand-held instrument. In certain embodiments, the pressure is between approximately 10 and 30 grams/30 mm². In certain embodiments, multiple images are captured under automated control using a step and repeat process.

In another embodiment, a method of diagnosing function of a human meibomian gland of the eyelid involves providing a diagnosis decision tree; focusing a camera on a surface of the eyelid containing an orifice of the meibomian gland; from the outer surface of the eyelid, applying adequate pressure to the eyelid to mimic the pressures applied to the meibomian gland during blinking of the eye, such pressure normally causing fluid within the meibomian gland to be expressed and to cause an occluded gland to exhibit physical deformities that are observable at the surface; from the outer surface of the eyelid, capturing a diagnostic image of the surface of the eyelid; rendering the diagnostic image to a viewable image display medium; relating observable conditions in the image with symptoms of compromised function by determining a proportion of meibomian glands that exhibit symptoms of compromised function to make a determination as to a severity of meibomian gland dysfunction.

In certain embodiments, the proportion of glands that exhibit symptoms of compromised function comprise glands that secrete fluid that is not clear. In certain embodiments, the proportion of glands that exhibit symptoms of compromised function comprise glands that secrete no fluid. In certain embodiments, the proportion of glands that exhibit symptoms of compromised function comprise glands that secrete no fluid and exhibit physical deformation at the meibomian gland orifice. In certain embodiments, the method further involves treating the occluded meibomian glands in an attempt to clear the occlusion; and repeating the focusing, applying pressure and capturing to capture a post treatment image to thereby document a degree of success of the treating. In certain embodiments, the pressure is applied using an instrument that applies a controlled amount of pressure in coordination with capturing the image. In certain embodiments, the pressure is applied using a hand-held instrument. In certain embodiments, the pressure is between approximately 10 and 30 grams/30 mm². In certain embodiments, multiple images are captured under automated control using a step and repeat process.

In another embodiment consistent with the present invention, an apparatus for imaging of mammalian meibomian glands of an eyelid, consistent with certain embodiments has an instrument that applies pressure to the eyelid adequate to mimic the pressures applied to the meibomian gland during blinking of the eye, such pressure normally causing fluid within the meibomian gland to be expressed and to cause an occluded gland to exhibit physical deformities that are observable at the surface. A camera focuses on a surface of the eyelid containing an orifice of the meibomian gland, so that the outer surface of the eyelid an image containing the physical deformities of the meibomian gland orifice can be captured when pressure is applied to the eyelid.

In certain embodiments, an image processor receives an output signal from the camera and processes the image to thereby electronically enhance the image. In certain embodiments, an electronic storage device stores the captured image. In certain embodiments, a display displays the captured image, or a printer or other rendering device renders the image. In certain embodiments, the instrument is a hand-held instrument. In certain embodiments, the instrument applies a controlled amount of pressure in coordination with capturing the image. In certain embodiments, the pressure is between approximately 10 and 30 grams/30 mm² In certain embodiments, a decision tree provides a reference for comparison of image characteristics to diagnose the condition of the meibomian glands. In certain embodiments, the decision tree defines symptoms of compromised function to make a determination as to a severity of meibomian gland dysfunction by determination of a proportion of the meibomian glands exhibiting symptoms of compromised function. In certain embodiments, a proportion of meibomian glands that exhibit symptoms of compromised function comprise those meibomian glands that do not produce clear fluid. In certain embodiments, the proportion of glands that exhibit symptoms of compromised function comprise glands that secrete fluid that is not clear. In certain embodiments, the proportion of glands that exhibit symptoms of compromised function comprise glands that secrete no fluid. In certain embodiments, the proportion of glands that exhibit symptoms of compromised function comprise glands that secrete no fluid and exhibit physical deformation at the meibomian gland orifice.

In another embodiment, an apparatus for imaging of mammalian meibomian glands of an eyelid, has a hand held tool to apply pressure to the eyelid adequate to mimic the pressures applied to the meibomian gland during blinking of the eye, such pressure normally causing fluid within the meibomian gland to be expressed and to cause an occluded gland to exhibit physical deformities that are observable at the surface. A camera focuses on a surface of the eyelid containing an orifice of the meibomian gland, so that the outer surface of the eyelid an image containing the physical deformities of the meibomian gland orifice can be captured as an image. A storage device stores the captured image; and a display displays the captured image.

In certain embodiments, an image processor, receives an output signal from the camera and processes the image to thereby electronically enhance the image. In certain embodiments, the pressure is between approximately 10 and 30 grams/30 mm². In certain embodiments, a decision tree that defines symptoms of compromised function to make a determination as to a severity of meibomian gland dysfunction by determination of a proportion of the meibomian glands exhibiting symptoms of compromised function. In certain embodiments, a proportion of meibomian glands that exhibit symptoms of compromised function comprise those meibomian glands that do not produce clear fluid. In certain embodiments, the proportion of glands that exhibit symptoms of compromised function comprise glands that secrete fluid that is not clear. In certain embodiments, the proportion of glands that exhibit symptoms of compromised function comprise glands that secrete no fluid. In certain embodiments, the proportion of glands that exhibit symptoms of compromised function comprise glands that secrete no fluid and exhibit physical deformation at the meibomian gland orifice.

In another embodiment, an apparatus for imaging of mammalian meibomian glands of an eyelid has a hand held tool to apply pressure between approximately 10 and 30 grams/30 mm$^2$ to the eyelid adequate to mimic the pressures applied to the meibomian gland during blinking of the eye, such pressure normally causing fluid within the meibomian gland to be expressed and to cause an occluded gland to exhibit physical deformities that are observable at the surface. A camera focuses on a surface of the eyelid containing an orifice of the meibomian gland, so that from the outer surface of the eyelid an image containing the physical deformities of the meibomian gland orifice can be captured. A storage device stores the captured image and a display displays the captured image; an image processor, receives an output signal from the camera and processes the image to thereby electronically enhance the image.

In certain embodiments, a decision tree defines symptoms of compromised function to make a determination as to a severity of meibomian gland dysfunction by determination of a proportion of the meibomian glands exhibiting symptoms of compromised function. In certain embodiments, a proportion of meibomian glands that exhibit symptoms of compromised function comprise those meibomian glands that do not produce clear fluid, glands that secrete fluid that is not clear, glands that secrete no fluid and glands that both secrete no fluid and exhibit physical deformation at the meibomian gland orifice.

Infrared Imaging

In general, infrared imaging can be divided into two distinct categories—optical imaging and infrared spectroscopy, or thermal imaging. Tomography can be used in many of the imaging techniques discussed by sectioning and reconstruction of a 3D image using software.

NIR Imaging

NIR optical imaging is an extension of visual light imaging, where the sample is illuminated with Near Infra Red (NIR) light (about 0.650-2.5 microns), either transmitted through the object, or reflected from the object, and the light is focused onto a typical red sensitive CCD camera (out to about 1.2 microns) to produce a monochromatic image. These images show the spatial resolution of structures, not the temperature profile. The spatial resolution of these images is proportional to the wavelength of light, so an image taken with 1 micron (NIR) wavelength light will have half the resolution of an image taken with 0.5 micron wavelength (green) light, all other things being equal. Penetration depths in human tissue of the IR illumination can vary with in the range of a few mm to a few cm.

NIR optical imaging can be accomplished using a suitable infrared light source and highly sensitive CCD (charge-couple device) camera that records light reflected from the eyelid. For example, NIR light from a tungsten-halogen bulb penetrates human tissue to a depth adequate to illuminate the meibomian glands. A portion of the light traveling through human tissue is absorbed by chromophores, or light-absorbing molecules, in the skin's layers. By beaming light onto the patient's eyelids and measuring reflected light, differences between light reflected by chromophores and other body tissues and the fluid and/or tissue of the meibomian glands can be visualized.

NIR cameras are readily available and have a penetration depth more than enough to see through eyelids. By use of optics of a typical slit lamp microscope that are able to pass NIR frequencies (and are suitably modified if necessary to pass NIR frequencies), NIR cameras can be used to image the meibomian glands. Illumination with NIR lighting can be either from behind the eyelid for transmission, or in front of the eyelid as illustrated below for reflected light imaging.

Figure 22:
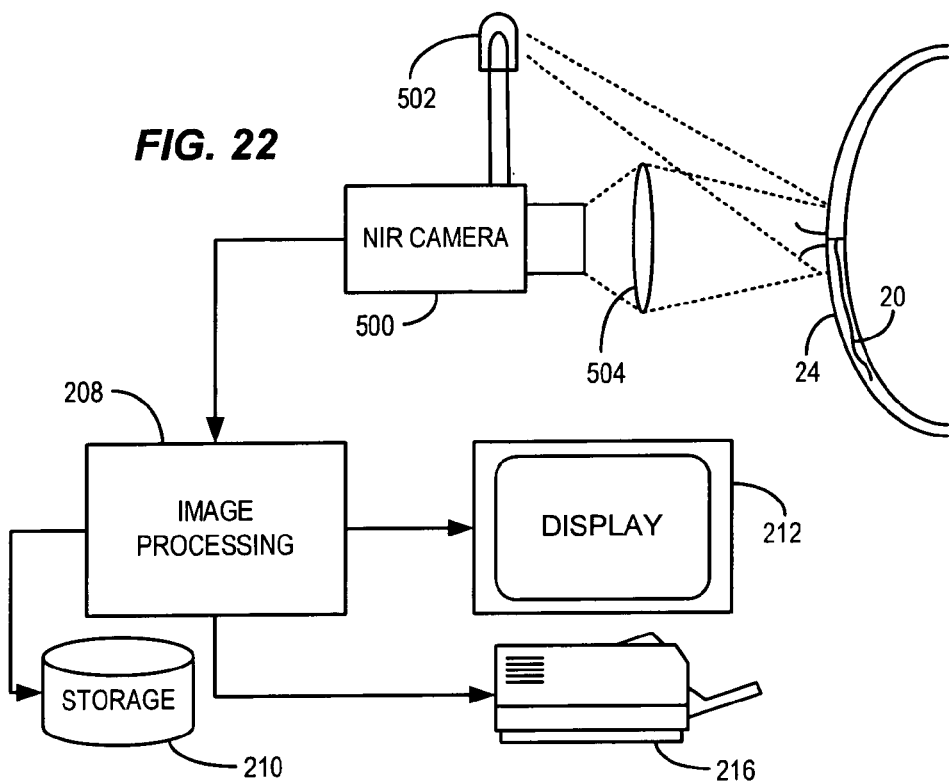
FIG. 22 illustrates an exemplary optical Infrared imaging system for imaging meibomian glands in a manner consistent with certain embodiments of the present invention.

Near Infrared imaging can be utilized to ascertain the condition and function of the meibomian glands as depicted in FIG. 22. NIR cameras, and in particular high resolution NIR photography, can be used to image the eyelid to some depth inside the tissue. The blood vessels located in the eyelid will be denser in areas outside the meibomian glands and the glands themselves will be filled with material which will have a different NIR response than the surrounding tissue. Using a High Resolution NIR camera should result in the ability to differentiate between the various tissue, the glands and material causing occlusion of the gland orifice.

In NIR imaging, the eyelids can be imaged using near infrared photography techniques, generally in the 0.650 to 2.50 micron wavelength to detect differences in the transmission or reflection of infrared light from the meibomian glands. This is in comparison to the 3-8 micron wavelength used in night vision infrared imaging, where thermal radiation from the body is the imaging energy.

In this process, a near infrared (NIR) camera 500 is used in conjunction with a NIR light source 502, through suitable magnification represented by 504, to capture an image of the eyelid (e.g., lower eyelid 24) and associated meibomian gland 20. The camera 500 may produce conventional optical photographic images that can either be developed and viewed or can be directed to an image processing computer 208 that can then process and possibly enhance (e.g., by use of pseudo-color color assignment techniques to assign different colors or color ranges to different fray levels emitted from the target image) the image. The image can then either be displayed on a display monitor 212, or stored on disk or other storage 210, or printed on a photographic quality printer 216 or any or all of the above. In addition to still NIR images, moving NIR images can similarly be captured in this manner to produce, for example, a pan across the eyelid in which individual frames can be captured and printed if desired.

In accordance with certain embodiments consistent with the present invention, the NIR camera may be based upon readily available high resolution NIR cameras. Either a conventional lens can be used with multiple images taken to image various areas of the eyelid, or a specially designed lens can be provided which provides for focus on the curved surface of the eye, and thereby compensate for the curvature of the eye.

An NIR camera can be utilized to image the eyelid to some depth inside the tissue. The blood vessels located in the eyelid will be denser in areas outside the Meibomian glands and the glands themselves will be filled with material which will have a different NIR response than the tissue around it. Using a sophisticated High Resolution NIR camera should be able to differentiate between areas of tissue and areas of glands. The wavelength and optics used for the NIR camera should be selected to provide suitable imaging of the meibomian glands and can be optimized by experimentation. Additionally, it may be advantageous to digitally process the resulting images to enhance the contrast level and/or assign coloration to distinguish between the NIR responses of the various tissues.

In addition to the NIR photography technique using a slit lamp microscope, imaging can be carried out using a suitable microscopic objective lens. As noted previously, the central duct of a meibomian gland is on the order of about 100 microns in diameter. Additionally, the glands are separated by approximately 1 mm and have an orifice on the order of approximately 0.1 mm (based upon a limited sampling of human subjects). The TABLE 1 below shows the resolution of objective lenses for light at 900 nm (0.9 microns) wavelength. Based upon these data, a microscopic objective lens having between about 60× and 20× magnification should be suitable for providing high resolution imaging of a meibomian gland. The field of view listed in TABLE 1 refers to the diameter of the viewable area of the sample.

TABLE 1

| Objective | 63× | 40× | 20× | 10× | 5× | 2.5× |
|---|---|---|---|---|---|---|
| Numerical Aperture | 1.32 | 0.75 | 0.5 | 0.3 | 0.15 | 0.075 |
| Resolution (microns) | 0.42 | 0.73 | 1.10 | 1.83 | 3.66 | 7.32 |
| Field of View (microns) | 317 | 500 | 1000 | 2000 | 4000 | 8000 |

It is further noted that the total image magnification can increased by a factor of 10× with a 10× eyepiece on the microscope, however the resolution is determined by the objective lens.

Thus, a method of near infrared (NIR) imaging of a meibomian gland involves illuminating the meibomian glands with NIR radiation using an NIR light source; focusing an NIR camera on a region of an eyelid containing the meibomian gland; making a first NIR image of the meibomian gland; applying a pressure suitable for simulating blinking pressure on the meibomian gland; optionally refocusing the NIR camera on the region of the eyelid containing the meibomian gland; and making a second NIR image of the meibomian gland while the pressure is being applied. The method is preferably carried out with the NIR camera having an objective of between about 60× and 20× at 900 nm wavelength.

IR Thermal Imaging

Figure 23:
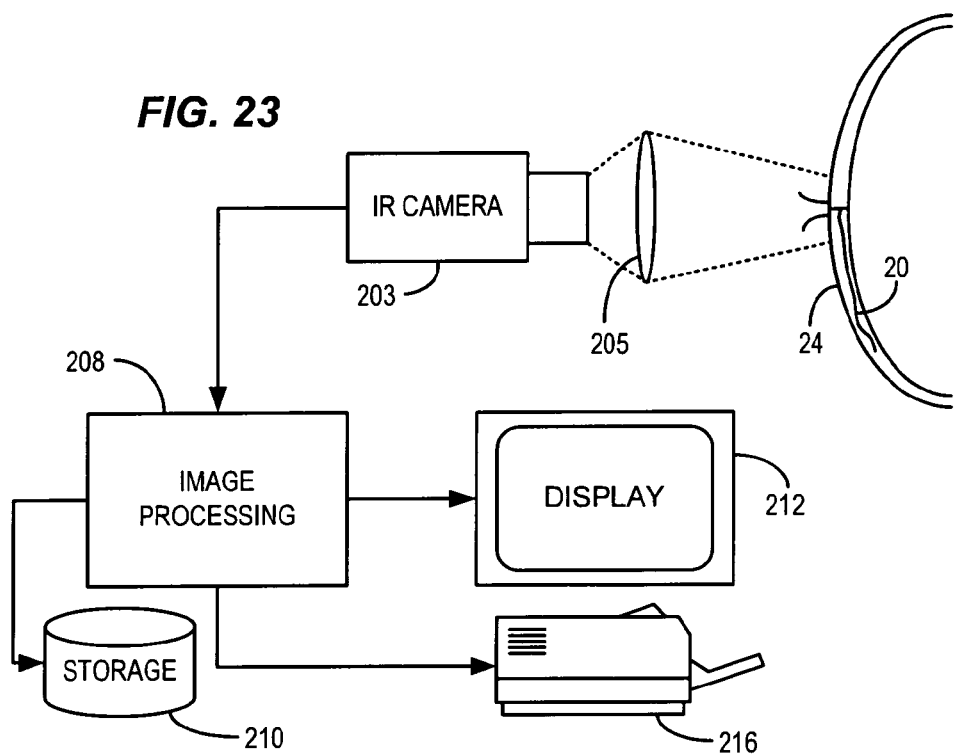
FIG. 23 illustrates an exemplary Infrared thermal imaging system for imaging meibomian glands in a manner consistent with certain embodiments of the present invention.

IR thermal imaging detects the IR emitted energy from the object being observed (2.5-18 micron wavelength range), and is a function of its temperature. The detector system, in accordance with certain embodiments, is made up of an array of bolometers that record the heat energy from different parts of the object. Detectors are usually divided into wavelength ranges, e.g. 4-6 microns (Mid. IR), 8-14 microns (Far IR). While spatial resolution is included in IR spectroscopy due to the regular array of bolometers in the detector, it is proportionately lower than with NIR optical images. The peak emission wavelength for the human body is about 10 microns. Once an image is captured by an IR camera, a pseudo color image can be readily constructed from the data showing the temperature differences between the parts of the image. Hence, the differences in temperature emitted by the meibomian glands and associated structures can be imaged using thermal IR imaging. FIG. 23 depicts a thermal IR image consistent with certain embodiments of the present invention.

Infrared imaging can also be utilized to ascertain the condition and function of the meibomian glands as depicted in FIG. 23. IR cameras, and in particular high resolution IR photography, can be used to image the eyelid to some depth inside the tissue. The blood vessels located in the eyelid will be denser in areas outside the meibomian glands and the glands themselves will be filled with material which will have a different IR response than the surrounding tissue. Using a High Resolution IR camera should result in the ability to differentiate between the various tissue, the glands and material causing occlusion of the gland orifice.

In this process, an infrared (IR) camera 203 is used, through suitable magnification represented by 205, to capture an image of the eyelid (e.g., lower eyelid 24) and associated meibomian gland 20. The camera 203 may produce either conventional photographic images that can be developed and viewed or can be directed to an image processing computer 208 that can then process and possibly enhance (e.g., by use of pseudo-color color assignment techniques to assign different colors or color ranges to different degrees of heat emitted from the target image) the image. The image can then either be displayed on a display monitor 212, or stored on disk or other storage 210, or printed on a photographic quality printer 216 or any or all of the above. In addition to still IR images, moving IR images can similarly be captured in this manner to produce, for example, a pan across the eyelid in which individual frames can be captured and printed if desired.

In accordance with certain embodiments consistent with the present invention, the IR camera may be based upon readily available high resolution IR cameras. Either a conventional lens can be used with multiple images taken to image various areas of the eyelid, or a specially designed lens can be provided which provides for focus on the curved surface of the eye, and thereby compensate for the curvature of the eye.

An IR camera can be utilized to image the eyelid to some depth inside the tissue. The structures within the eyelids including the blood vessels, meibomian glands, acini, lipids, skin tissue, and blockages located in the eyelid will emit thermal radiation at varying intensities. Using a sophisticated High Resolution IR camera should be able to differentiate between areas of tissue and areas of glands. The wavelength and optics used for the IR camera should be selected to provide suitable imaging of the meibomian glands and can be optimized by experimentation. Additionally, it may be advantageous to digitally process the resulting images to enhance the contrast level and/or assign coloration to distinguish between the IR responses of the various tissues.

Figure 24:
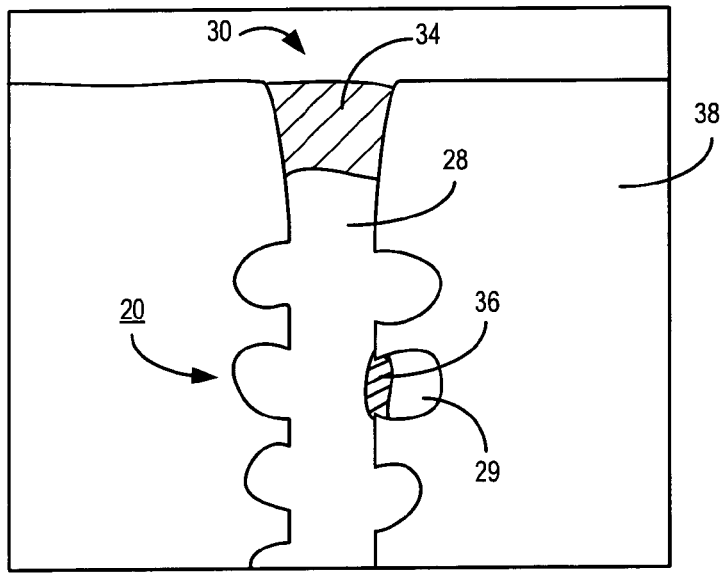
FIG. 24 is an example representation of an IR image of an occluded meibomian gland consistent with certain embodiments of the present invention.

FIG. 24 depicts an exemplary image that might be obtained via optical near infrared photography or infrared thermal imaging. In this image, simplified for purposes of this illustration to demonstrate only anatomical features of interest, it is expected that an image of an occluded meibomian gland will emit IR radiation at differing wavelengths at the location of the occluded orifice 30 (at 34) and the occluded acini 29 (at 36) than would be expected at a normally functioning gland. Thus, the image can be processed to present a different color of the image at orifice 30 and occlusion 34 and acini 29, central duct 28 and occlusion 36 than of the remainder of gland 20 and surrounding tissue of the eyelid 24. Note that while FIG. 24 illustrates a single meibomian gland, this is for illustrative purposes only since one, more or all of the glands or the entire eyelid or both eyelids may be imaged in a single image or multiple images in various embodiments.

Figure 25:
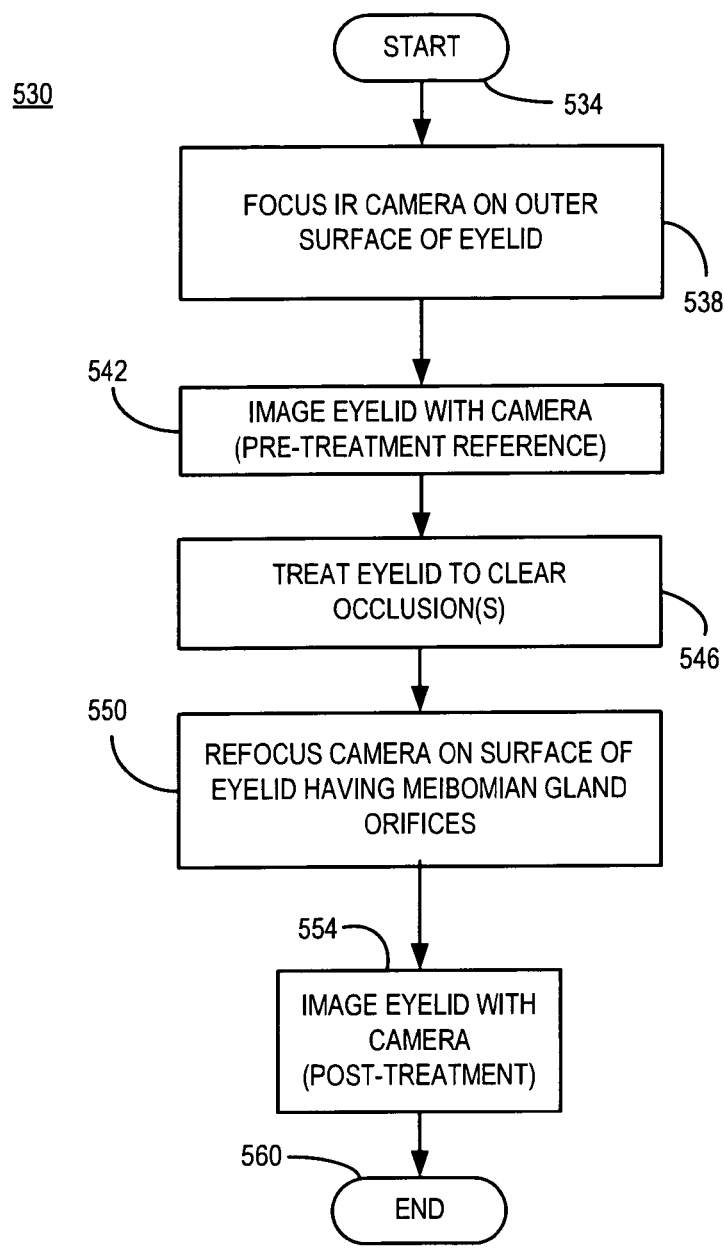
FIG. 25 is a flow chart depicting an exemplary method of use for the IR visualization techniques consistent with embodiments of the present invention, but with simple modification is applicable to any of the techniques described herein.

FIG. 25 depicts an exemplary process 530 for imaging the meibomian glands using infrared photography in a manner consistent with certain embodiments of the present invention starting at 534 after which the IR or NIR camera is focused on the surface of the eyelid (or on the MG where possible). (For other imaging techniques, analogous processes can be utilized with suitable modification e.g., using a visible light camera or ultrasound device rather than an IR camera.) An image is then created at 542 to create a pre-treatment reference image. This image may be processed as described above, either by fully automated means of with the assistance of manual intervention to highlight significant attributes by color assignment or enhancement. The glands may then be treated using any suitable treatment mechanism at 546. The effectiveness of the treatment can then be evaluated by imaging the eyelid in the same manner as previously by refocusing the IR camera on the eyelid at 550 and re-imaging the eyelid using infra-red photography and enhancement as needed at 554. The process ends at 560. As has been previously discussed, the application of pressure may also be used during the imaging process to augment the process and determine the state of function of the glands. Either still or moving images may be used in the imaging process, and pressure can be applied as described above to mimic blinking pressures.

As noted above, in one embodiment, the IR camera may be fitted with a lens designed to correct for the curvature of the human eye. While there is variation in the size and curvature of the human eye, a lens designed for the average can likely be used across the spectrum of eye sizes with adequate performance.

As is the case with any microscopic imaging process, the image should preferably be produced under circumstances wherein the object being imaged is as stable as possible. In this case, the head can be stabilized in a conventional manner using conventional ophthalmologic chin and forehead braces as are used in conventional ophthalmologic exams, with the examination braces fitted with suitable infrared photography instruments as described above.

Thus, a method of infrared (IR) imaging of a meibomian gland involves providing an IR camera; focusing an IR camera on a region of an eyelid having the meibomian gland to be imaged; making a first IR image of the meibomian gland; applying a pressure suitable for simulating blinking pressure on the meibomian gland; optionally refocusing the IR camera on the region of the eyelid containing the meibomian gland; and making a second IR image of the meibomian gland while the pressure is being applied.

As is the case with any microscopic imaging process, the image should preferably be produced under circumstances wherein the object being imaged is as stable as possible. In this case, the head can be stabilized in a conventional manner using conventional ophthalmologic chin and forehead braces as are used in conventional ophthalmologic exams, with the examination braces fitted with suitable infrared photography instruments as described above.

Trans-Illumination

A new form of trans-illumination can be used to image the meibomian glands in one of several ways. In one variation illuminating light can be directed at the outer anterior surface of the eyelid at an angle, with imaging also taking place from the outer anterior surface of the eyelid. This is referred to as oblique illumination. In a second variation, light can be directed from behind the eyelid through the eyelid with imaging taking place through the outer surface of the eyelid. In a third variation, the surface is illuminated from the front in a manner such that the light source partially blocks the image being recorded, with averaging, adding or otherwise combining of multiple images being used to produce a complete image. In each instance, the meibomian gland is illuminated in order to visually examine the gland using light transmitted through the eyelid tissue. The eyelid can then be imaged using still or moving photography (visible light, NIR or IR or other suitable light wavelength) in a manner similar to that depicted above.

Figure 26:
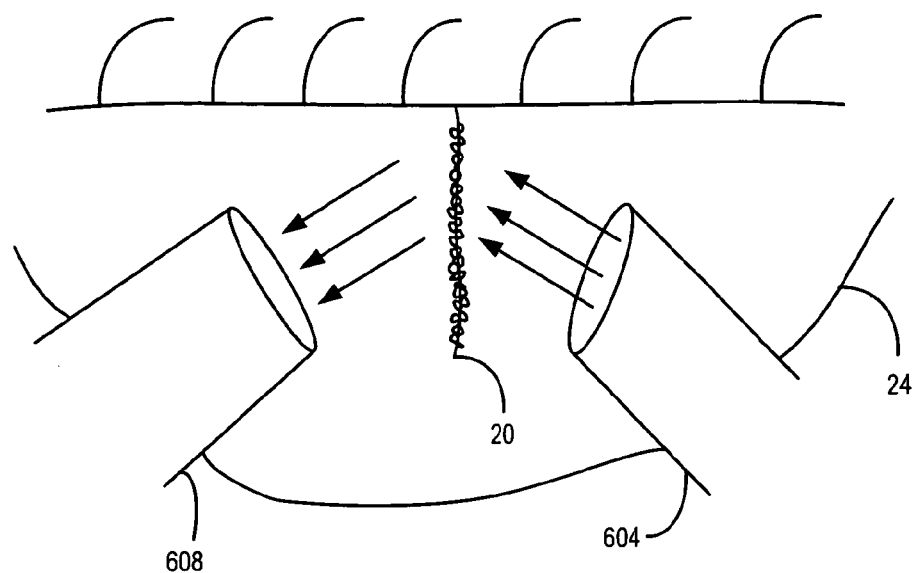
FIG. 26 is an illustration of an exemplary system for oblique illumination for trans-illumination imaging of an eyelid in a manner consistent with certain embodiments of the present invention.
Figure 27:
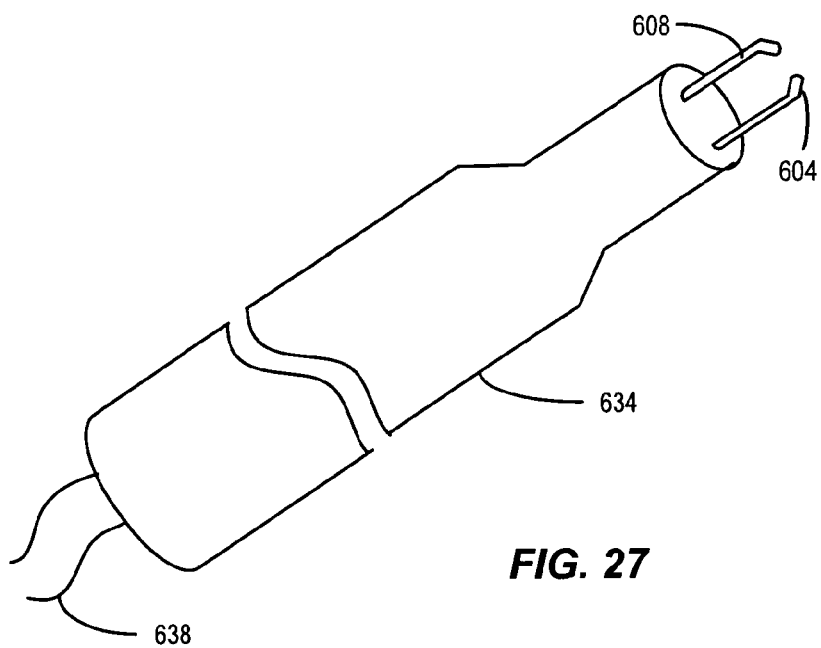
FIG. 27 depicts an exemplary hand-held instrument for manual imaging of a portion of the eyelid using oblique illumination consistent with certain embodiments of the present invention.

The first variation of this technique is depicted in FIGS. 26-27. With reference first to FIG. 26 the basic concept of oblique trans-illumination for imaging the eyelid and associated glands is depicted. In this illustration, light is directed toward the eyelid at a suitable angle to cause a section of the flesh of the eyelid to be trans-illuminated by transmission of light through the flesh itself. In this case, a light source 604 is simply depicted as a light conducting fiber that directs light to a desired location of the outer surface of the eyelid. A light receiving element (which again is depicted as an optical fiber) 608 is positioned on the same outer surface of the eyelid in order to image the trans-illuminated area of the eyelid and one or more meibomian glands such as 20. In certain embodiments, this technique can be used to completely manually probe the eyelid as with the manual probe depicted in FIG. 27, while in other embodiments; the eyelid can be scanned by moving the probe (light source and receiver) in an organized manner (e.g., under computer control) over the eyelid and electronically assembling a larger image of the eyelid.

In accordance with various embodiments, the source fiber 604 and the receiver fiber 608 can be individually manipulated, or may be contained in a single hand-held probe 634 as depicted in FIG. 27. In such a probe, both fibers can be optically isolated and stress relieved in a single cable 638 that is attached to a combined light source 612 and optical receiver unit 616 as shown separately in FIG. 28. The tips of the probe can be of such design as to capture the image of a small (e.g., approximately circular, oblong, rectangular, etc.) region of the eyelid using a single imaging element or a small array of imaging elements (e.g., CCDs), or a vertical or horizontal stripe of the eyelid so as to capture the length of an individual or set of meibomian glands by using a rectangular array of imaging elements, or any other suitable array of elements. Additionally, a full or partial image of the eyelid can be assembled electronically by stitching, adding, averaging or otherwise electronically combining overlapping images using photographic stitching or combining techniques.

Figure 28:
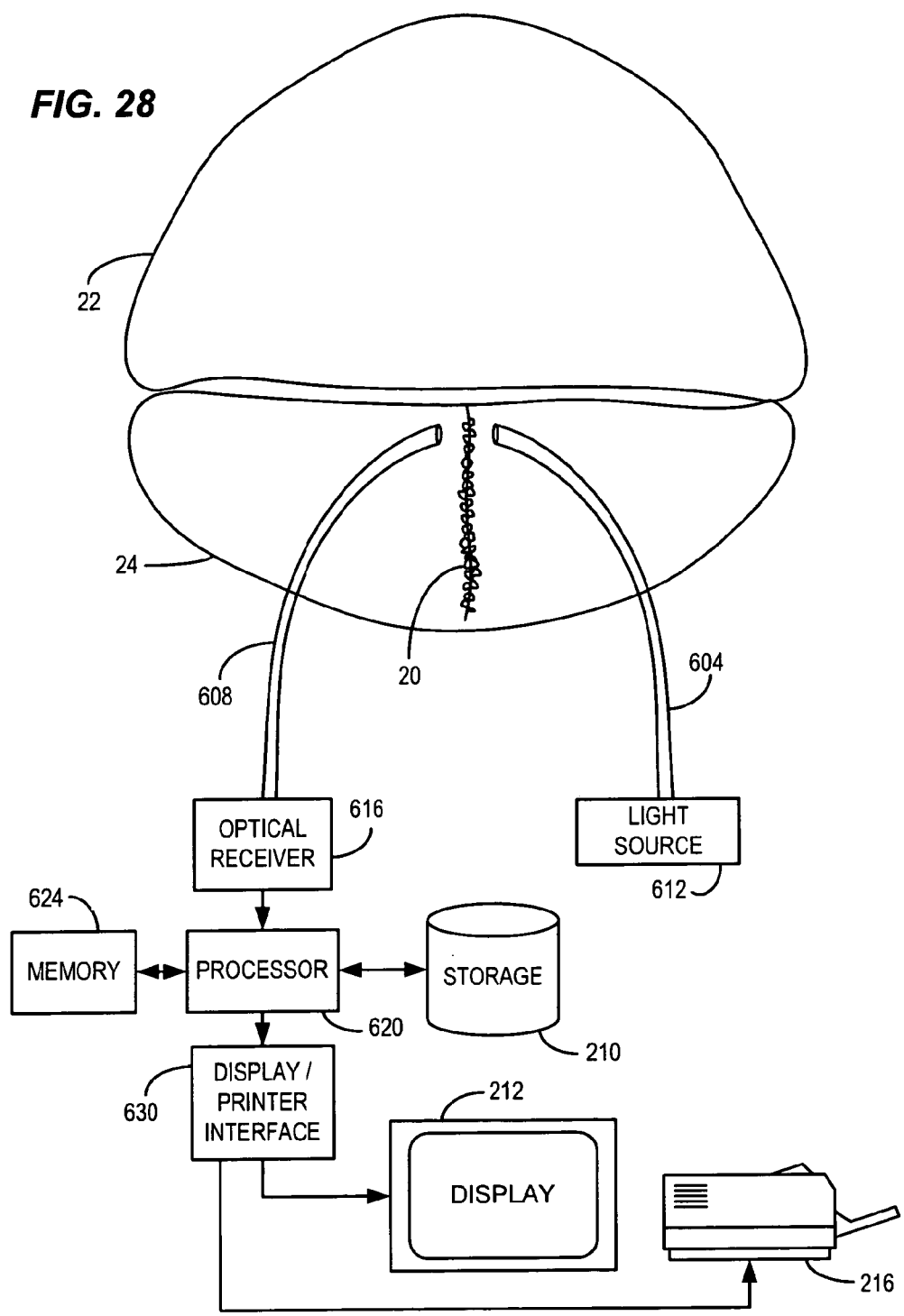
FIG. 28 is an illustration of a trans-illumination system consistent with certain embodiments of the present invention.

FIG. 28 depicts a more complete image of the imaging setup in which fiber 604 directs light from a suitable light source such as a light emitting diode, laser, incandescent or halogen source 612 to the eyelid. The resulting image is received via light conduit 608 at an optical receiver 616 which delivers a digital representation of the image to a processor such as a microcomputer 620 having associated working memory 624 and mass storage such as disc drive storage 210. The image can be stored at storage 210 for later retrieval, processing or enhancement. The image can also be viewed in real time or at a later time on display 212, or can be printed on printer 216, each of which is connected to the processor 620 via a suitable display and/or printer interface 630.

In certain embodiments, as described previously, the light source and optical receiver can be moved across the eyelid in an organized manner using an X-Y (or X-Y-Z) controller and a suitable servo motor arrangement (not shown in this illustration) under control of the processor 620 in order to scan a larger surface. Scanning the eyelid can be accomplished manually or by use of an X-Y control system as illustrated. In such an embodiment, the light source 612 and optical receiver 616 may be scanned across the eyelid in a suitable pattern to produce a full X-Y scan under control of X-Y scan controller 658 driving a servo arrangement 662, while high resolution camera 650 records the results.

Figure 29:
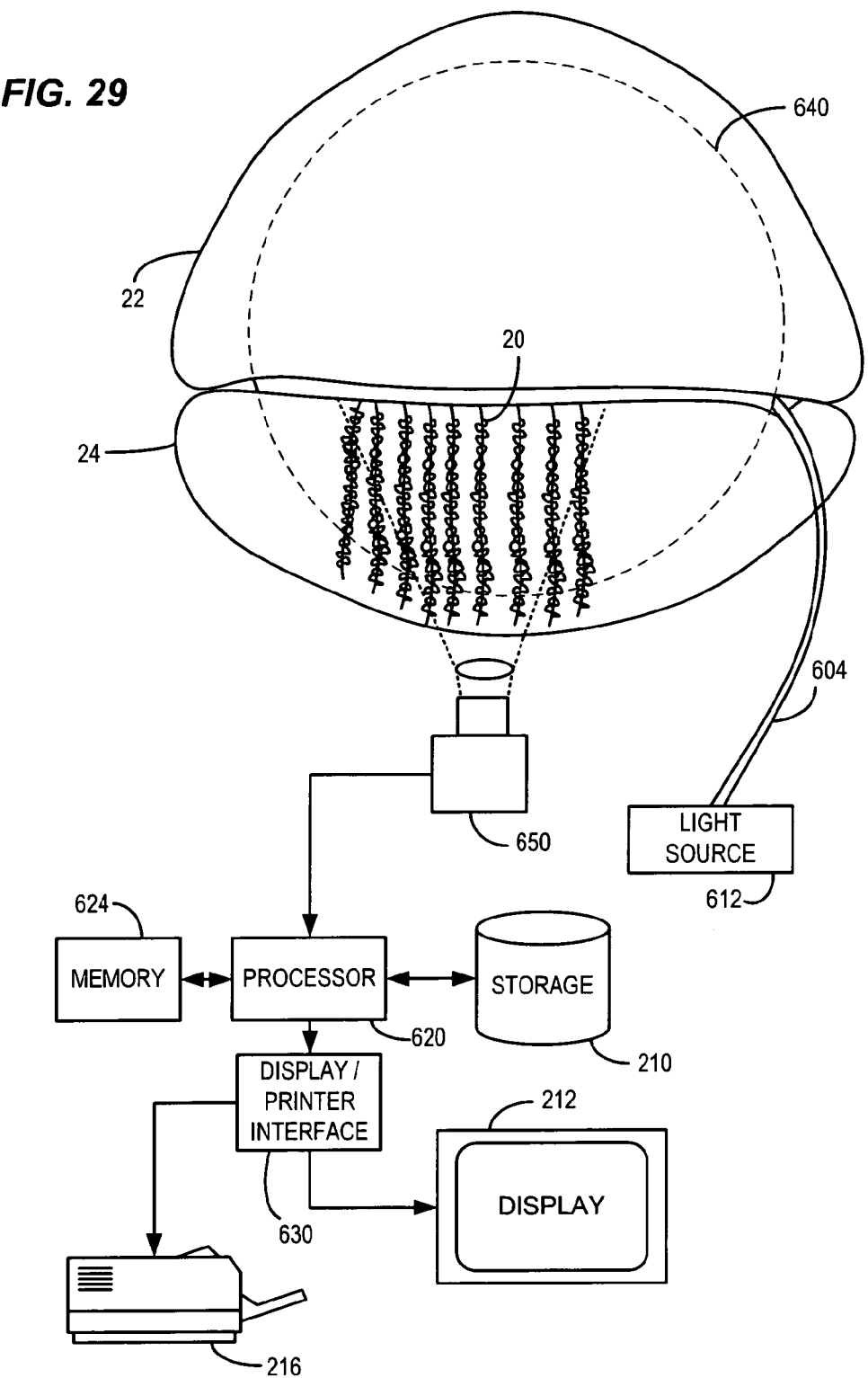
FIG. 29 is an illustration of an exemplary rear trans-illumination system consistent with certain embodiments of the present invention.

In another variation of the trans-illumination technique, depicted in FIG. 29, a device similar to a contact lens 640 is temporarily placed in the eye to act as a source of light that is fed by light source 612 via fiber 604. Fiber 604 is shown as illuminating the lens at an edge, but could also illuminate the lens near the center or from multiple locations without limitation in order to shine light through the eyelid from behind. This contact lens 640 can resemble a small eye shield similar to a scleral lens. A high resolution camera 650 can then be used to image the eyelid. Preferably, the contact lens has a reflective back side to protect the eye from exposure to high intensity light, coupled to a frosted lens element that scatters the light directed thereto by the light fiber 604 which is optically coupled to the frosted lens element. Multiple sizes of the lens can be provided to approximately accommodate eyes of various sizes, but need not be a perfect fit since the duration of need for installation of the lens against the eye is short term, and should result in minimal discomfort. Local anesthetic can also be used to minimize discomfort.

The lens 640 is illuminated by light passing through fiber 604 so that light is thereby passed from the posterior surface of the eyelid through the eyelid itself to illuminate the interior surface of the eyelid for imaging. This produces an image of the interior of the eyelid that can be captured in much the same manner as an image produced by shining a bright flashlight through a human hand (wherein, bones are readily visible through the flesh). Light of various colors or color combinations (including visible, UV, IR, NIR or combinations thereof) can be used in this embodiment.

Therefore, the present trans-illumination techniques can provide more consistent results with greater patient comfort than the technique in current use. In addition, automatic image capture and analysis can be incorporated. In this embodiment, a light source built into a small eye shield 640 similar to a scleral lens as described above provides the illumination source. Then high resolution camera 650 is used to visualize the resulting image. Various techniques can be used to increase the signal to noise ratio under low light conditions. Some of these techniques can produce motion artifacts in the image that should be noted in considering or image processing the output image. Image processing can be utilized to minimize such artifacts.

Figure 30:
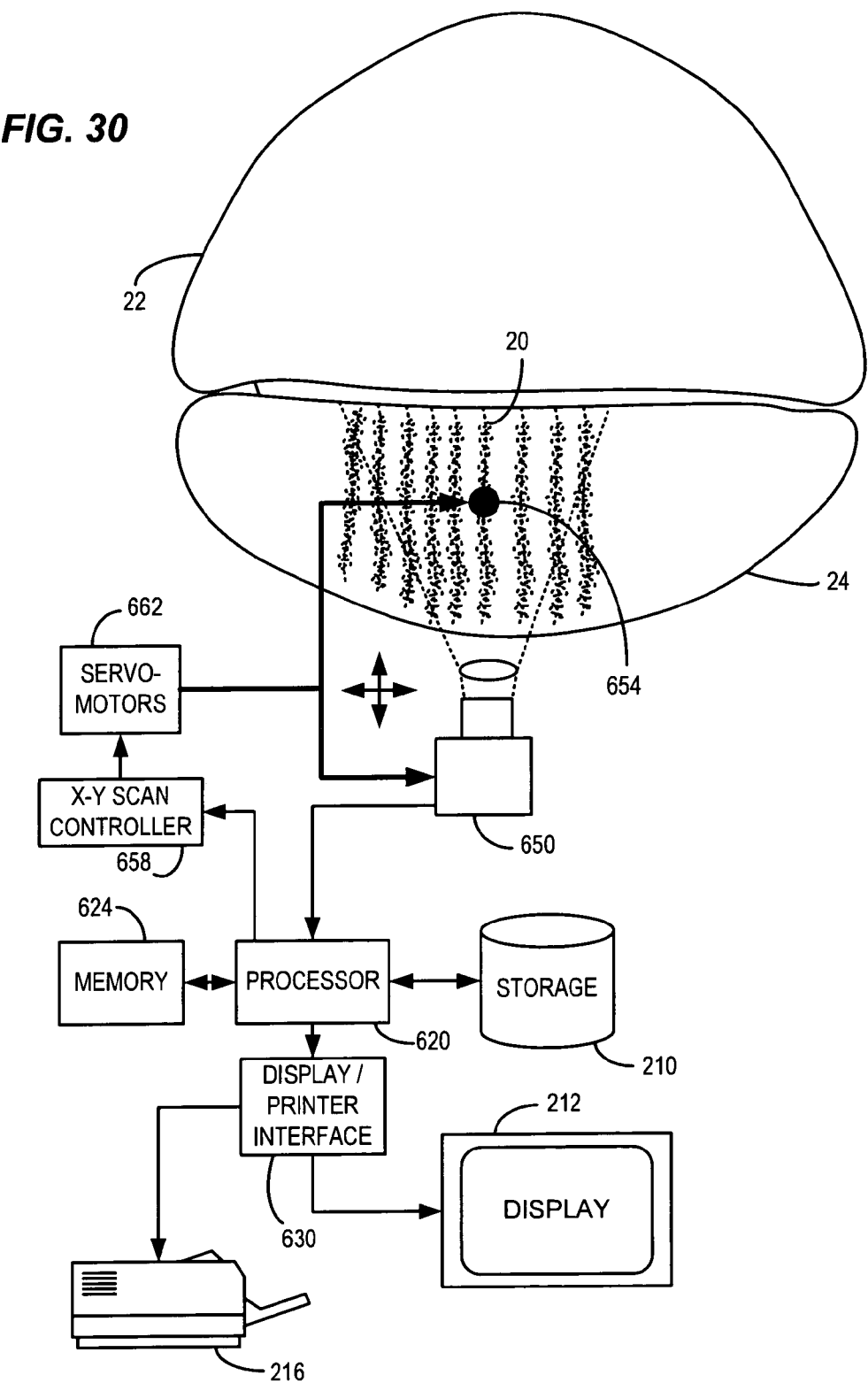
FIG. 30 depicts another exemplary trans-illumination technique consistent with certain embodiments of the present invention.

In a third alternative embodiment, as depicted in FIG. 30, an LED light source (or other suitable light source or light conduit therefrom) 654 can be placed close to or in contact with the outside of the eyelid (e.g., 24). The light source 654 is then manually or automatically scanned across the eyelid in a suitable pattern to produce a full X-Y scan under control of X-Y scan controller 658 driving a servo arrangement 662, while high resolution camera 650 records the results. The various image frames taken during the scan are then combined (e.g., stitched, averaged or added) together at processor 620 resulting in a composite trans-illuminated image. Alternately, the image of the light source can be subtracted from the resulting images. The theory behind this technique is similar to shining a flashlight on your hand and looking at the hand from the same surface as the light source is illuminating. You can see the tissue around the flashlight but you cannot see through the flashlight itself because it is blocking your field of view. However, if you move the flashlight around and record images at many positions, it is then possible to eliminate the flashlight body from your image by combining all of the resulting images together. Further image processing may also be carried out to enhance the resultant image. For example, in one embodiment, image recognition techniques can be used to recognize the shape of light source 654, and subtract that image from each image. Data from other images can then be inserted into the image from which the light source is subtracted. The process may be potentially further enhanced by experimentation with various illumination wavelengths.

In the above example, light is provided directly in front of the camera, while in prior examples, light was provided at the side of the camera or behind the eyelid. Hence, it will be evident that the light source can be placed in any suitable location with respect to the eyelid and the camera in order to produce trans-illumination of the meibomian gland or glands without limitation.

As with any light scattering approach, resolution using trans-illumination may be inferior to certain other approaches, but may be cost effective and adequate to identify at least fully occluded meibomian glands. In addition, the resultant image may include motion artifacts that should be considered in evaluation of the images, or that can be processed out of the images.

Thus, in one embodiment consistent with the present invention, a method of imaging a mammalian meibomian gland or other section of an eyelid involves shining a light on the outer surface of the eyelid in order to trans-illuminate a portion of the eyelid with oblique illumination; and from the outer surface of the eyelid, capturing an image of trans-illuminated portion of the eyelid.

In certain embodiments, the captured image is stored in an electronic storage medium and/or displayed on a video display. In certain embodiments, the shining and capturing are repeated at an adjacent location of the outer surface of the eyelid. In certain embodiments, the images from the first and adjacent locations are combined. In certain embodiments, the combining includes stitching, adding, or averaging the images from the first and adjacent locations to produce a resultant image of a larger area of the eyelid. In certain embodiments, the light includes infrared light radiation and capturing the image is carried out using infrared photography. In certain embodiments, the light includes visible light radiation and capturing the image is carried out using visible light photography. In certain embodiments, a computer readable storage medium can store instructions which, when executed on a programmed processor, carry out these methods.

In another embodiment, a method of imaging a mammalian patient's meibomian gland or other section of an eyelid of an eye involves placing a contact lens in contact with the eye; having the patient close the eye; illuminating the contact lens to generate light emitting from the lens through the eyelid from the posterior surface of the eyelid; and from the outer surface of the eyelid, capturing an image of a trans-illuminated portion of the eyelid. In certain embodiments, the captured image is stored in an electronic storage medium and/or displayed on a video display or otherwise rendered. In certain embodiments, the method further involves repeating the illumination and capturing of an image at a second location on the eyelid, and processing the images to produce a single composite image. In certain embodiments, the light includes infrared light radiation and capturing the image is carried out using infrared photography. In certain embodiments, the light includes visible light radiation and capturing the image is carried out using visible light photography. In certain embodiments, a computer readable storage medium can store instructions which, when executed on a programmed processor, carry out these methods.

In another embodiment, a method of imaging a mammalian meibomian gland or other section of an eyelid involves placing a light source at a first position adjacent an outer surface of the eyelid in order to trans-illuminate a portion of the eyelid from an outer surface thereof; from the outer surface of the eyelid, capturing a first image of trans-illuminated portion of the eyelid, the first image containing at least a portion of the light source; repositioning the light source to a second position adjacent an outer surface of the eyelid in order to trans-illuminate a portion of the eyelid from an outer surface thereof; from the outer surface of the eyelid, capturing a second image of trans-illuminated portion of the eyelid, the second image containing at least a portion of the light source; and computing a composite of the first and second image to produce a resulting image.

In certain embodiments, a computer readable storage medium can store instructions which, when executed on a programmed processor, carry out these methods. In certain embodiments, the computing of the composite image is carried out by a process of averaging, stitching or adding the first and second images. In certain embodiments, a composite image is computed by subtracting a light source obstruction from the image. In certain embodiments, the resulting image is stored in an electronic storage medium and/or displayed on a video display or otherwise rendered In certain embodiments, the light source includes an infrared light radiation source and capturing the images is carried out using infrared photography. In certain embodiments, the light source includes a visible light radiation source and capturing the images is carried out using visible light photography.

In another embodiment consistent with the present invention an apparatus for imaging a portion of a mammalian eyelid has a light source suitable for directing light to a portion of the outer surface of the eyelid using oblique illumination in order to trans-illuminate the portion of the eyelid. An optical receiver is provided that is suitable for receiving light transmitted through a portion of the eyelid and producing an output signal related to characteristics of the trans-illuminated portion of the eyelid, the light receiver receiving light from the outer surface of the eyelid. An image processor receives the output signal and captures an image from the light receiver.

In certain embodiments, an electronic storage device stores the captured image. In certain embodiments, a display displays the captured image. In certain embodiments, the light source directs light to the portion of the outer surface of the eyelid via a first optical fiber In certain embodiments, the optical receiver receives light from the outer surface of the eyelid via a second optical fiber. In certain embodiments, the light source directs light to the portion of the outer surface of the eyelid via a first optical fiber, and the optical receiver receives light from the outer surface of the eyelid via a second optical fiber, and the first and second optical fibers are positioned in a fixed geometric relationship with one another. In certain embodiments, the first and second optical fibers are positioned to direct light at a specified angle and receive the light at the specified angle as measured from a plane approximation of the surface of the eyelid. In certain embodiments, the first and second optical fibers are commonly contained in a single handpiece that holds the first and second optical fibers in the fixed geometric relationship with one another. In certain embodiments, multiple adjacent locations of the outer surface of the eyelid are imaged In certain embodiments, a processor combines the images from the multiple adjacent locations. In certain embodiments, a processor stitches the images from the multiple adjacent locations to produce a resultant image of a larger area of the eyelid. In certain embodiments, a processor sums the images from the multiple adjacent locations. In certain embodiments, the light source comprises an infrared light source and wherein the optical receiver is compatible with infrared light. In certain embodiments, the light source comprises a visible light source and wherein the optical receiver is compatible with visible light.

In another embodiment, an apparatus for imaging a portion of a mammalian eyelid has a light source. A contact lens is configured to receive light from the light source and direct the light through an eyelid from posterior to anterior surface to thereby trans-illuminate the eyelid, when the light source illuminates the contact lens. A camera records an image of the eyelid as it is trans-illuminated. In certain embodiments, an image processor, receives an output signal from the camera and processes the output signal to enhance the image. In certain embodiments, an electronic storage device stores the captured image. In certain embodiments, a display displays the captured image. In certain embodiments, the light source includes an infrared light source and wherein the camera is compatible with infrared light. In certain embodiments, the light source includes a visible light source and wherein the camera is compatible with visible light.

In another embodiment, an apparatus for imaging a portion of a mammalian eyelid has a light source configured to direct light through an eyelid from an anterior surface to thereby trans-illuminate the eyelid. A camera records an image of the eyelid as it is trans-illuminated. A positioning mechanism automatically positions the light source at a plurality of locations adjacent the eyelid and record a plurality of images at each of said plurality of locations using the camera. A processor averages the plurality of images to produce a resultant image.

In certain embodiments, an electronic storage device stores the resultant image. In certain embodiments, a display displays the resultant image. In certain embodiments, the light source comprises an infrared light source and wherein the camera is compatible with infrared light. In certain embodiments, the light source includes a visible light source and wherein the camera is compatible with visible light.

Optical Coherence Tomography (OCT)

Optical Coherence Tomography is a known tomographic technique that uses a comparison of a minor reflection to interference patterns of light waves reflected from tissue being imaged to form a tomographic image. This technique provides approximately 2-4 millimeters of penetration into tissue with sub-micrometer axial and lateral resolution when using wide bandwidth light sources (e.g., white light, lasers and LEDs) by use of low-coherence interferometry.

Figure 31:
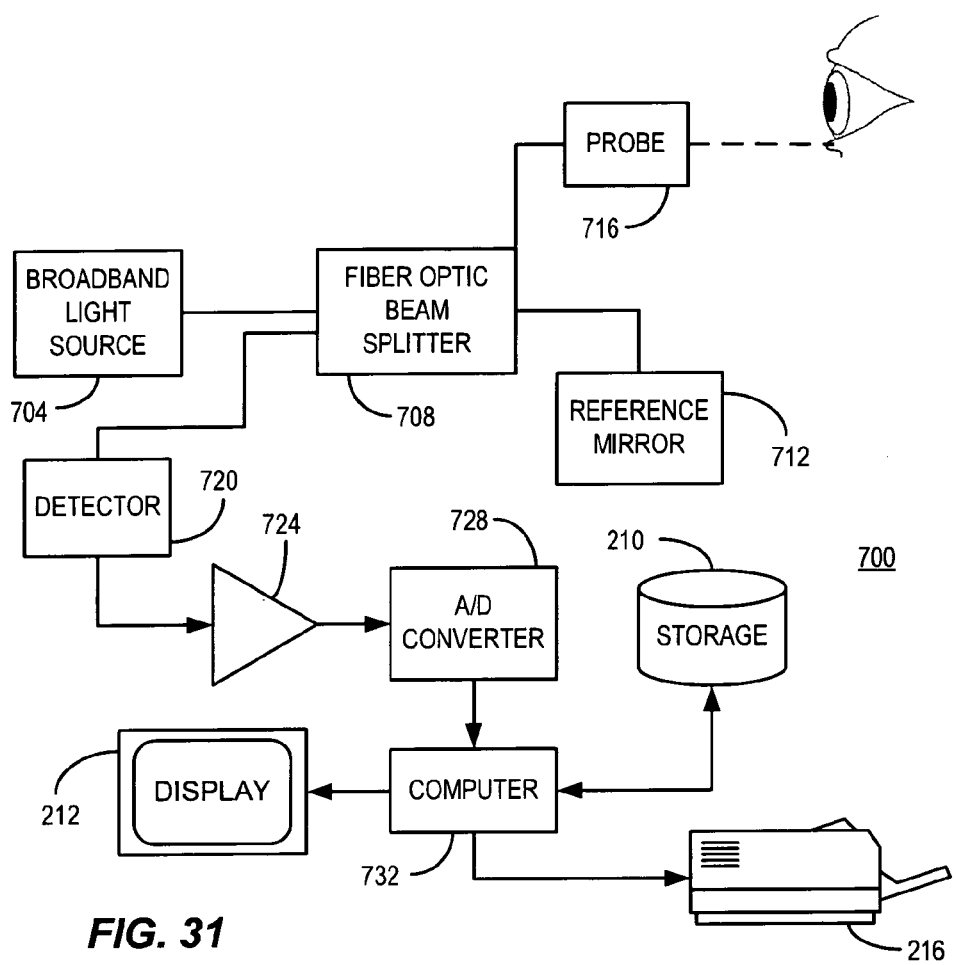
FIG. 31 is a block diagram of an OCT imaging system consistent with certain embodiments of the present invention.

FIG. 31 depicts an exemplary OCT system 700 which employs a broadband light source 704 to supply light to a fiber optic splitter 708. Once the light is split at 708, two beams of light are provided, one to a reference mirror 712 and the other to a probe 716. The distance from the beam splitter 708 to the reference mirror can be adjusted to provide axial scanning (depth), while lateral (x or y) scanning can be achieved by movement of the probe or a mirror used in reflecting light within the probe. The backscattered light received by the probe from the tissue being imaged combines with the reflection from the reference minor (after traveling the same optical distance) to produce interference patterns. The minor can be scanned to produce a reflectivity profile of the tissue sample that can be converted to a usable image.

The images from the probe and the mirror are received at detector 720 that converts the light image into an electrical signal which may then be filtered (filter not shown) and amplified by an amplifier 724. The amplified signal is converted from analog to digital at A/D converter 728 for tomographic processing by computer 732 in order to produce an image that can be stored at 210, displayed at 212 or printed at 216.

As is known in the art, OCT systems can be configured to produce a reflectivity profile known as an A-scan, a cross-sectional tomograph called a B-scan as well as a C-scan image that presents a face-on view. Other scans are also possible. Such images are dependent upon the scanning operation carried out, the probe mechanism used and the imaging engine running on computer 732. The imaging engine may be used to process the images in the time domain, frequency, spatially encoded frequency domain or time encoded frequency domain using known algorithms.

Owing to the shallow imaging depth possible using OCT (i.e., approximately 2 to 4 mm maximum) and the typical meibomian gland depth of approximately 3 to 4 mm from the front surface of the eyelid, imaging the meibomian gland will often push the limits of OCT technology if imaging is attempted from the anterior surface of the eyelid. However, the extremely high resolution is a desirable attribute for identifying the occlusions and other anomalies of the meibomian glands. In order to address this issue, several approaches can be taken. The eyelids can be imaged from the lid margin surface of the eyelid, i.e., the surface that presents the gland orifice (e.g., the upper surface of the lower eyelid), or can be imaged from the posterior surface of the eyelid. In the case of imaging from the posterior surface, one approach is to first invert the eyelid in order to image it from the rear. In either case, the depth of penetration is adequate to obtain substantial information for diagnosis and documentation of the condition of the meibomian glands. For patients with thinner eyelids, the image may even be taken from the front surface of the eyelid. Additionally, penetration depth can be increased by use of light in the infrared range so that an image can be captured from the outer surface of the eyelid.

Since it is desired to only image the eyelids and in particular the meibomian glands, it follows that custom algorithms can be developed which enhances the glands appearance. Such algorithms can be developed by use of tissue characterization for tissues encountered in the eyelids combined with Doppler imaging (which normally images blood flow but could be used to image the flow of Meibomian secretion) and Harmonic imaging. There are many known techniques for harmonic imaging but the use of harmonic imaging on Meibomian glands has never been done. Harmonic imaging works by detecting the non-linear response of the sample being imaged. The normal meibomian secretion is believed to have a much weaker non-linear response than the surrounding tissue and this characteristic can be used to make the glands more distinguishable when imaged. Since the eyelids are not moving (unless the person blinks), multiple images can be processed and a composite picture can be generated utilizing many scans. Each of these techniques alone or some combination of these techniques can be used to visualize these small glands.

Thus, a method of imaging a mammalian meibomian gland of an eyelid using Optical Coherence Tomography involves directing light from a beam splitter to scan a surface of the eyelid; directing light to a reference minor from the beam splitter; detecting an interference pattern between light reflected from the reference minor and light reflected from the surface of the eyelid; and generating a tomographic image from the interference pattern, wherein the tomographic image represents structures between approximately 2-4 mm below the surface of the eyelid.

In certain embodiments, the surface of the eyelid is a rear surface of the eyelid. In other embodiments, the surface of the eyelid is the surface bearing the meibomian gland orifices. In certain embodiments, the process further involves inverting the eyelid prior to directing the light from the beam splitter to scan the surface. In certain embodiments, the eyelid is a lower eyelid of a human. In certain embodiments, the scan can be any one of an A-scan, a B-scan and a C-scan or any other suitable scanning technique. In certain embodiments, the process further involves processing the tomographic image in a domain selected from the group consisting of the time domain, the frequency domain, the spatially encoded frequency domain and the time encoded frequency domain. In certain embodiments, the tomographic image in an electronic storage medium and/or rendered on a display or as a printed photographic image. In certain embodiments, a computer readable storage medium stores instructions which, when executed on a programmed processor, carry out any of the above methods.

In another embodiment, a method of imaging a human meibomian gland of an eyelid using Optical Coherence Tomography involves inverting the human eyelid to expose a rear surface thereof; directing light from a beam splitter to scan the rear surface of the eyelid; directing light to a reference mirror from the beam splitter; detecting an interference pattern between light reflected from the reference minor and light reflected from the rear surface of the eyelid; generating a tomographic image from the interference pattern, wherein the tomographic image represents structures between approximately 2-4 mm below the surface of the eyelid; and storing the tomographic image in an electronic storage medium.

In certain embodiments, the scan is one of an A-scan, a B-scan and a C-scan or any other suitable scanning techniques. In certain embodiments, the process further involves processing the tomographic image in a domain selected from the group consisting of the time domain, the frequency domain, the spatially encoded frequency domain and the time encoded frequency domain. In certain embodiments, the tomographic image in an electronic storage medium and/or rendered on a display or as a printed photographic image. In certain embodiments, a computer readable storage medium stores instructions which, when executed on a programmed processor, carry out any of the above methods.

In another embodiment, a method of imaging a human meibomian gland of an eyelid using Optical Coherence Tomography involves inverting the human eyelid to expose a rear surface thereof; directing light from a beam splitter to scan the rear surface of the eyelid; directing light to a reference mirror from the beam splitter; detecting an interference pattern between light reflected from the reference minor and light reflected from the rear surface of the eyelid; generating a tomographic image from the interference pattern, wherein the tomographic image represents structures between approximately 2-4 mm below the surface of the eyelid; storing the tomographic image in an electronic storage medium; and rendering the tomographic image on a video display as a photographic image. In certain embodiments, the tomographic image in an electronic storage medium and/or rendered on a display or as a printed photographic image. In certain embodiments, the scan is one of an A-scan, a B-scan and a C-scan. In certain embodiments, the process further involves processing the tomographic image in a domain selected from the group consisting of the time domain, the frequency domain, the spatially encoded frequency domain and the time encoded frequency domain.

In each case, the light may be visible light or light in the near ultraviolet or ultraviolet spectrum.

VHF Ultrasound Imaging

Conventional ultrasound devices are well known in the art, but have not been successfully used to image the meibomian glands. Such imaging presents unique challenges that are not generally faced in other ultrasound imaging. The contour of the eyelid should be addressed in such imaging, and the signal processing to be used addresses some of the physical properties associated with the meibomian glands and eyelids. Hence, the process should be tuned to an optimal frequency, an appropriate depth, and appropriate software algorithms are utilized to image the appropriate section of the eyelids to visualize the meibomian glands so as to visualize and quantify obstruction.

VHF Ultrasound has been generally defined as ultrasound using frequencies greater than 25 MHz or 50 MHz (depending upon whose definition is used). However, actual use of VHF Ultrasound to date has been limited to devices operating at a maximum of 50-60 MHz range, and more commonly in the 25-30 MHz range. This is useful in imaging the anterior regions of the human eye, for example, due to enhanced resolution obtainable in this range. As frequencies used for ultrasound are increased, higher resolution can be achieved. Unfortunately for most applications, the penetration depth of the target tissue being imaged is sacrificed in exchange for such resolution. At 50 MHz, penetration is dramatically reduced over, for example 10 MHz, but resolution improves by approximately a factor of five to achieve resolution of approximately 30 and 60 microns axial and lateral respectively. Recently, transducers capable of use at 80-200 MHz have been documented, and are commercially available, but their use in ultrasound imaging applications has been largely unexplored, since in this frequency range, only a few millimeters of penetration depth is possible.

"Ultrasonography of the Eye and Orbit", second edition, by D. Jackson Coleman, Ronald H. Silverman, Frederic L. Lizzi and Mark J. Rondeau, © 2006 by Lippincott Williams and Wilkins, 530 Walnut St., Philadelphia, Pa. 19106 provides a treatment of the role of ultrasound in the imaging and diagnosis of the eye. However, this text as well as the literature in general appears to be devoid of any mention of how one might use ultrasound to image the meibomian glands.

As previously noted, the typical human eyelid is less than 5 mm in thickness, and is most often less than 4 mm in thickness. The upper eyelid contains approximately 25-30 meibomian glands while the lower eyelid contains approximately 20-25 meibomian glands. In most instances, the meibomian glands are situated within the eyelid approximately ⅔ of the way from the front to the rear of the eyelid. The central duct of a small sample of glands that have been measured are roughly 100 microns in diameter (with a great deal of variation anticipated since only a limited number of glands have actually been measured at this writing). This presents a rather unusual imaging problem in that the gland is quite small, located at a very sensitive part of the body and requires high resolution imaging to actually observe. Moreover, the eyelid follows the contour of the eye, and can only be minimally compressed or flattened to do imaging operations. Imaging these glands is further complicated by the relatively small size of the glands and lack of clear reference points to identify one particular gland and distinguish it from other glands, and by patient movement during visual examinations at high magnifications.

For imaging meibomian glands of the human eyelid, a maximum penetration depth of approximately 4 to 5 mm of skin and glandular tissue is required with a resolution of 0.5 to 10 microns within the meibomian gland. However, due to the small size of the glands and location within the eyelid, conventional VHF ultrasound is clearly inadequate. While current VHF ultrasound imaging equipment conventionally operates at 25 MHz to 60 MHz, application of VHF ultrasound to image the meibomian glands will likely be more advantageously imaged at frequencies much greater than 60 Mhz. In particular frequencies in the range of about 80 or 100 MHz to about 160 Mhz should be able to be effectively utilized to image a full range of normal thicknesses of human eyelids.

Higher frequencies result in higher the attenuation of sound through the tissue. If the maximum depth is 5 mm one can calculate the maximum frequency to obtain this depth will be approximately 160 MHz. This calculation estimates attenuation in eyelid tissue of approximately 0.7 db/Mhz-cm and assumes that the meibomian gland secretion has a relative scattering of about 40 db as compared to adjacent tissue and also assumes that the system signal to noise ratio is at least about 100 db. These are all reasonable assumptions with the current state of the art. Relatively high power may be required to achieve the desired signal to noise ratio, but this is also within the state of the art.

Figure 32:
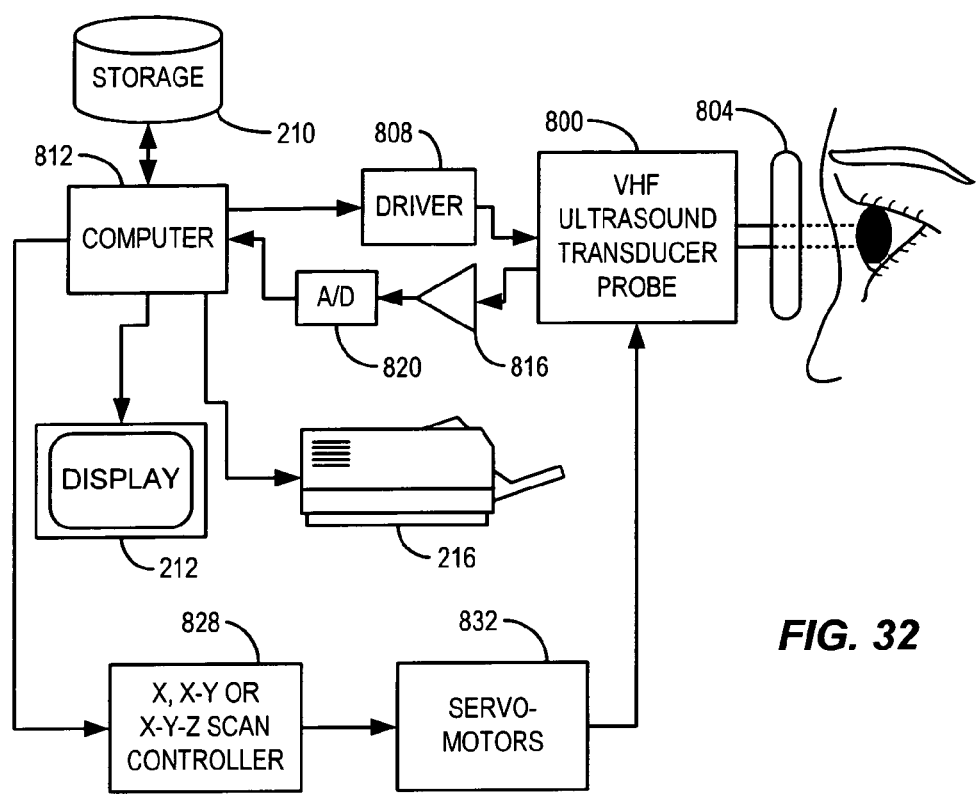
FIG. 32 is a VHF Ultrasound system consistent with certain embodiments of the present invention.

FIG. 32 illustrates a VHF Ultrasound apparatus suitable for imaging the meibomian glands in accordance with certain embodiments consistent with the present invention. In such an arrangement, a VHF transducer probe 800 is placed in contact with the eyelid (and in certain embodiments, also with the eyeball as will be explained) via a coupling medium depicted schematically as 804 (which is actually contacting both the probe and the eye in a known manner). This coupling medium may be, for example, a saline or other liquid bath or gel, or a liquid or gel filled pouch that provides an efficient interface for transmission of the VHF Ultrasound waves into and out of the eyelid and eyeball. Given the short penetration depth and high resolution, air bubbles should be avoided to assure a clear image.

The transducer (or transducers) in probe 800 is driven by a driver circuit 808 which is controlled by computer 812 under program control in a more or less conventional manner, with the transducer being operational in the 80 or 100 MHz to 160 MHz range. Reflected VHF sound waves are transmitted back through coupling medium 804 and are converted by the transducer or transducers in probe 800 into electrical currents that pass-through transmit/receive switch and are amplified by amplifier 816, converted to digital signals at A/D converter 820 for delivery to computer 812 for processing. Computer 812 generates images from the received sound waves and can store, print and or display them on storage device 210, printer 216 and display 212 in a conventional manner.

In accordance with certain embodiments consistent with the present invention, the computer 812 further controls an X-Y, or X-Y-Z scan controller 828 that drives servo motors 832 to manipulate the physical position of the probe 800. Alternatively or additionally, computer 812 may also be used to electronically steer a transducer array forming a part of the probe 800 in order to direct the transducer to scan a particular area of the target eyelid or eyeball using known electronic steering techniques.

Figure 33:
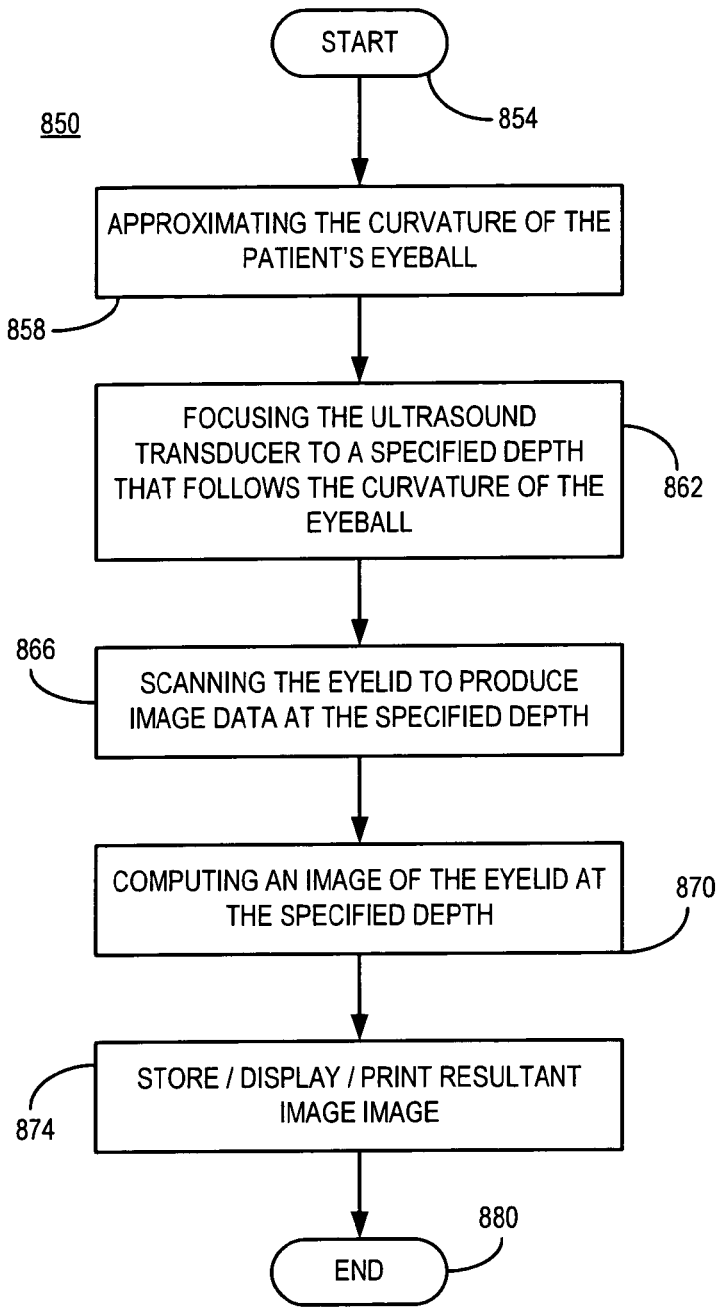
FIG. 33 is a method of imaging the meibomian glands using VHF Ultrasound in a manner consistent with certain embodiments of the present invention.

Referring now to FIG. 33, a process 850 consistent with certain embodiments of the present invention is depicted for identifying an appropriate region of the eyelid for imaging in order to capture the meibomian glands. In process 850, a method of generating an ultrasonic image of the glands within the eyelid is described starting at 854 wherein a surface area of the eyelid is identified and scanned in a manner such that the resulting image is parallel to the surface of the eye ball. At 858, the process first approximates the curvature of the surface of the patient's eyeball. This can be accomplished by electronically or mechanically moving the transducer in a "cross" pattern across the lid then algorithmically detecting the boundary between the eye and lid. Detection of such a boundary is a simple matter due to the adjacent epidermal tissue and distinct line continuity that will show up in the scanned image. Alternatively, the boundary can be identified by moving the transducer probe in a "cross" pattern across the lid then having the user trace the boundary between the eye ball and the eye lid. In a further alternative, the transducer probe can be automatically moved using the mechanical X-Y or X-Y-Z servo stage arrangement in a pattern across the eyelid and automatically detecting the eyelid to eyeball boundary by scanning the patient with the eyelid open and then with the eye lid closed.

In one embodiment, the appropriate focus point can be determined as follows: while keeping the eyelid closed, the patient is asked to squeeze their eyes shut several times. The system then records the tissue which is moving (the eyelid) and the tissue which is not moving (the eyeball) and calculates the curvature of the eyeball.

Next, at 862, the ultrasound transducer is focused (assuming it is of variable focus) on a specified depth for imaging the meibomian glands. This may be avoided for fixed focus systems. This is a predictable depth from the front or rear of the eyelid when the eyelid thickness is known, and can be readily followed once the curvature of the eyeball is established. This focus depth can be accomplished electronically to focus the transducer to a specific depth which follows the curvature of the eye with an offset into the eyelid to account for the eyelid thickness. An annular array transducer can be used using a phased array transducer or using a fixed focus transducer which can be mechanically moved closer or further from the eye.

At 866, the eyelid is scanned, for example, by moving the transducer in a grid pattern across the eyelid. This can be done with an X-Y-Z stage and a fixed focus transducer, or by using an X-Y stage and an annular array electronically focused transducer, or by using an X (or Y) stage and a phased array or linear array transducer. Once the image has been scanned at 866, computer 812 can compute an image of the eyelid at the specified depth in order to render an image of the meibomian glands at 870. Such an image represents an approximately oblique spheroidal slice parallel to the eye ball surface at the selected depth from the eyeball into the eyelid. The image is created by combining the return echoes which have been sampled at the predetermined depth and combining them to form the image in a conventional manner. In addition, by use of several imaging depths, a thicker image can be generated to thereby create a 3D rendering of the spherical slice.

It is noted that for imaging the meibomian glands:

maximum penetration depth of less than about 5 mm is needed;

resolution of 0.5 to 25 microns is desired with ideal resolution in the 0.5 to 10 micron range to be able to clearly image the inner working of the meibomian glands;

higher frequency will provide better resolution, with the sacrifice of penetration-penetration depth considerations being quite shallow for imaging the meibomian glands;

focus can be fixed or variable on about the first 5 mm of thickness, or perhaps only about 2-4 mm of thickness;

due to the shallow depths and small imaging target, the curvature of the eye should be approximated for most accurate imaging; and as VHF frequency transducers between about 80 or 100 MHz and 160 MHz provide the resolution adequate to provide useful images of the glands. Such transducers can readily be implemented into the probe mechanism to further enhance resolution and improve diagnosis.

The present techniques can be implemented in both hand held probe mechanisms as well as stationary machines in which the patient's head is secured (e.g., by chin and forehead rests). In the hand held version, absolute positioning can be ascertained by the use of an X-Y-Z positioning device which does not control the position but simply reports it. This can be accomplished by attaching the ultrasonic transducer to a mechanical arm with sensors detecting the position and orientation of the transducer as it is moved along the eyelid. The position data can then be combined with the ultrasonic data to create a 3-Dimensional image. Alternately, a wireless position sensor or so called "chirper" could also be utilized. Such devices are in use in other imaging systems and can be readily adapted to the present ultrasound system.

In the event of use of a hand-held probe, another embodiment uses a curved half moon shaped transducer array that follows an approximate oblique spheroid shape to approximate the curvature of the eyeball. Electronic steering and focusing can be used to produce imaging of various segments of the eyelid. This approach will produce an image which is simply a slice through the eyelid perpendicular to the eye ball. The resulting image depends on the orientation of the probe. When the probe is oriented normal to the eyeball then the user will see circles representing each meibomian gland at a particular depth from the orifice. When the probe is oriented near parallel to the surface of the eyeball then positioning will be critical and difficult but theoretically the user would see a cross section of a single meibomian gland. However, it should be noted that any method which does not have a way of detecting or setting the absolute X-Y-Z transducer position on the eyelid may not be able to determine which gland the user is actually imaging, without establishment of a reference.

The ultrasound probe can be 1) is fixated to the eyelid either by placement against the forehead or nose, 2) fixation in relation to the eyelid with placement against the eye socket, 3) contoured or radius shape to match the radius of the eyelid as all people will have some form of positive radius for their eyelid.

It is also noted that application of pressure to the eyelid during imaging can be used to mimic the action of blinking by the patient. The transducer contact with the patient may be adequate to simulate such pressure, or may actually exceed this pressure which is generally on the order of 10-30 gm/30 mm$^2$.

Figure 34:
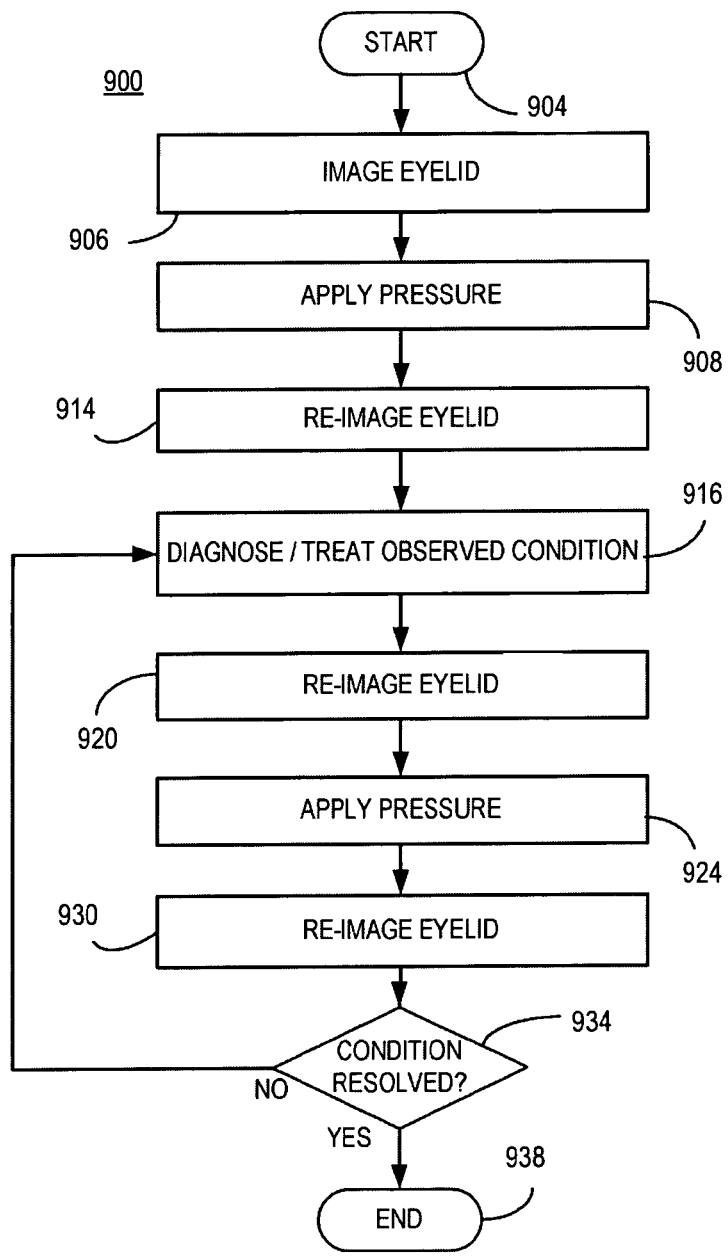
FIG. 34 is a flow chart depicting a method of use for the visualization techniques consistent with embodiments of the present invention.

FIG. 34 depicts an exemplary comprehensive imaging and treatment process 900 that can be used for diagnosis and treatment of MGD using any of the imaging techniques disclosed herein starting at 904. At 906, the eyelid is imaged without any application of force to the eyelid itself. Process 906 may not be possible since the contact with the eyelid by the imaging device may meet or exceed the pressure of blinking. At 908, pressure is applied to the eyelid and the eyelid is re-imaged at 914 while the pressure is present. Once the imaging is completed, a diagnosis can be made and an appropriate course of treatment can be carried out in an effort to resolve the condition observed. The effectiveness of the treatment can then be evaluated by re-imaging the eyelid at 920 without pressure, as well as applying pressure at 924 and re-imaging the eyelid under pressure at 930. A determination can then be quantitatively made at 934 as to the effectiveness of the treatment and either the process can end at 938 or further diagnosis and treatment carried out at 916. It is noted that for ultrasound imaging, processes 908 and 920 may not be possible since the contact with the eyelid may meet or exceed the pressure of blinking. However, the application of pressure in this application may permit imaging of the MG while in the act of secreting when the gland is at least partially properly functioning and not fully occluded. Many variations are possible including only imaging with or without pressure applied to the eyelid at any stage according to the preferences of the physician, experiences with the patient, imaging technique used or other factors.

Thus, in accordance with certain embodiments, a method of imaging a mammalian meibomian gland of an eyelid covering an eyeball using Very High Frequency (VHF) Ultrasound involves approximating a curvature of the eyeball; focusing a VHF ultrasound transducer having frequency between 80 and 160 MHz to a first specified depth below an anterior surface of the eyelid approximating a depth of the location of the meibomian glands of between 2 and 5 mm, and that follows the approximated curvature of the eyeball; scanning the eyelid at the first specified depth following the approximated curvature of the eyeball; and computing an image of the eyelid at the specified depth.

In certain embodiments, the method further involves focusing the VHF Ultrasound transducer to a second specified depth below an anterior surface of the eyelid differing from the first approximate depth, but still between 2 and 5 mm in depth, of the location of the meibomian glands and that follows the approximated curvature of the eyeball; scanning the eyelid at the second specified depth following the approximated curvature of the eyeball; and computing a three dimensional image of the eyelid from the scans carried our at the first and second specified depths. In certain embodiments, the focusing involves a fixed focus transducer either electronically or by mechanical movement. In certain embodiments, the focusing comprises adjusting a variable focus. In certain embodiments, the scanning is carried out under control of a computer controlled scanner such as an X scanner, a Y scanner, an X-Y scanner or an X-Y-Z scanner. In certain embodiments, the ultrasound transducer is fixated to the eyelid either by placement against a portion of the patient's face In certain embodiments, the ultrasound transducer comprises an array of ultrasound transducers. In certain embodiments, the ultrasound transducer is contoured in shape to approximate the radius of the eyelid. In certain embodiments, a computer readable storage medium stores instructions which, when executed on a programmed processor, carry out these methods.

In another embodiment, a method of imaging a mammalian meibomian gland of an eyelid covering an eyeball using Very High Frequency (VHF) Ultrasound involves approximating a curvature of the eyeball; focusing a VHF ultrasound transducer having frequency between 80 and 160 MHz to a first specified depth below an anterior surface of the eyelid approximating a depth of the location of the meibomian glands of between 2 and 5 mm, and that follows the approximated curvature of the eyeball; scanning the eyelid at the first specified depth following the approximated curvature of the eyeball; focusing the VHF Ultrasound transducer to a second specified depth below an anterior surface of the eyelid differing from the first approximate depth, but still between 2 and 5 mm in depth, of the location of the meibomian glands and that follows the approximated curvature of the eyeball; scanning the eyelid at the second specified depth following the approximated curvature of the eyeball; and computing a three dimensional image of the eyelid from the scans carried our at the first and second specified depths.

In certain embodiments, the focusing involves adjusting a variable focus. In certain embodiments, the ultrasound transducer comprises an array of ultrasound transducers. In certain embodiments, the ultrasound transducer is contoured in shape to approximate the radius of the eyelid. In certain embodiments, the scanning is carried out under control of a computer controlled scanner such as an X scanner, a Y scanner, an X-Y scanner and an X-Y-Z scanner. In certain embodiments, a computer readable storage medium stores instructions which, when executed on a programmed processor, carry out these methods.

In another embodiment, a Very High Frequency (VHF) Ultrasound imaging system for imaging mammalian meibomian glands of an eyelid of an eye has a VHF ultrasound transducer that couples VHF Ultrasound waves at 80-160 MHz to and from the eyelid. The VHF ultrasound transducer is driven to produce the VHF Ultrasound waves. The reflected VHF Ultrasound waves are converted to a computer readable signal. A computer receives the computer readable signal, wherein the computer is programmed to: compute an approximate curvature of the eye; control the VHF ultrasound transducer to produce a scan of the eyelid at a depth between 2 and 5 mm depth into the eyelid that approximates a location of the meibomian glands while following the computed approximate curvature of the eye; and calculate an image from the scan at the prescribed depth within the eyelid.

In certain embodiments, the computer is further programmed to: scan the eyelid at second specified depth between 2 and 5 mm following the approximated curvature of the eyeball; and calculate a three dimensional image of the eyelid from the scans carried our at the first and second specified depths. In certain embodiments, the VHF ultrasound transducer is contoured in shape to approximate the radius of the eyelid. In certain embodiments, the scanning is carried out under control of a computer controlled scanner such as an X scanner, a Y scanner, an X-Y scanner and an X-Y-Z scanner. In certain embodiments, the ultrasound transducer is realized as an array of ultrasound transducers.

In order to use any of the above embodiments of imaging techniques and apparatus, it is possible (likely in many instances) that the patient will be more comfortable and thus the imaging process can proceed easier if a topical anesthetic is applied to the outer surfaces of the eyes and to the eyelids. This facilitates greater comfort when the images are created and while the eyelids are manipulated where such manipulation is needed. Moreover, such anesthetic may be beneficial in minimizing patient blinking.

Those skilled in the art will appreciate, upon consideration of the present teachings, that any of the above techniques described can be used to provide reference, pre-treatment and post treatment images of one or more meibomian glands or the eyelid so as to provide diagnosis and records of treatment success.

Those skilled in the art will recognize, upon consideration of the above teachings, that certain of the above exemplary embodiments are based upon use of a programmed processor. However, the invention is not limited to such exemplary embodiments, since other embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Certain embodiments described herein, are or may be implemented using a programmed processor executing programming instructions that are broadly described above in flow chart form that can be stored on any suitable electronic or computer readable storage medium and/or can be transmitted over any suitable electronic communication medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping can be added and/or enhanced and variations can be made in user interface and information presentation without departing from certain embodiments of the present invention. Such variations are contemplated and considered equivalent.

Software and/or firmware embodiments may be implemented using a programmed processor executing programming instructions that in certain instances are broadly described above in flow chart form that can be stored on any suitable electronic or computer readable storage medium (such as, for example, disc storage, Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies) and/or can be transmitted over any suitable electronic communication medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping can be added and/or enhanced and variations can be made in user interface and information presentation without departing from certain embodiments of the present invention. Such variations are contemplated and considered equivalent.

While certain illustrative embodiments have been described, it is evident that many alternatives, modifications, permutations and variations will become apparent to those skilled in the art in light of the foregoing description.

What is claimed is:

1. A method of evaluating and treating dry eye wherein the flow of naturally occurring secretion to an eye is reduced or stopped due to the presence of an obstruction of a meibomian gland in an eyelid having a plurality of meibomian glands comprising:
    imaging at least one meibomian gland of the plurality of meibomian glands to diagnose a condition of the at least one meibomian gland;
    treating the at least one meibomian gland to remove an obstruction from at least a portion of a central duct of the at least one meibomian gland located below an orifice of the at least one meibomian gland;
    re-imaging the at least one meibomian gland, wherein the re-imaging comprises imaging the at least a portion of the central duct of the at least one meibomian gland that is located below the orifice of the at least one meibomian gland to verify that the obstruction has been removed; and
    applying a force to eyelid; wherein at least one of the imaging and the re-imaging is carried out with the force applied to the eyelid.

2. The method of claim 1, wherein at least one of the imaging and the re-imaging is carried out with the force applied to the eyelid as a result of natural blinking of the eyelid.

3. The method of claim 1, wherein at least one of the imaging and the re-imaging is carried out with the force applied to the eyelid that mimics pressure applied during blinking of the eyelid.

4. The method of claim 1, wherein the imaging at least a portion of the central duct of the at least one meibomian gland comprises imaging the central duct.

5. The method of claim 1, wherein the imaging at least a portion of the central duct of the at least one meibomian gland comprises imaging at least one acinus.

6. The method of claim 1, wherein the imaging at least a portion of the central duct of the at least one meibomian gland comprises imaging the central duct and at least one acinus to determine if there is an obstruction in the at least one acinus or at a junction of the central duct and the at least one acinus.

7. The method according to claim 1, wherein the imaging is carried out using one of a group comprising VHF ultrasound imaging, OCT imaging, NIR optical imaging, infrared thermal imaging, trans-illumination imaging, and visible light photographic imaging of a surface of the eyelid.

8. The method of claim 1, wherein the imaging and re-imaging are carried out using an imaging process selected from a group comprising VHF ultrasound imaging, OCT imaging, NIR optical imaging, infrared thermal imaging, trans-illumination imaging, and visible light photographic imaging of a surface of the eyelid.

9. The method according to claim 7, wherein an image resulting from the imaging is processed by assignment of pseudocolors to the image.

10. The method according to claim 1, wherein the imaging is carried out using VHF ultrasound, and where VHF frequency is between 80 and 160 MHz.

11. The method according to claim 1, wherein the imaging is carried out using OCT imaging.

12. The method according to claim 1, wherein the imaging is carried out using NIR optical imaging in a 0.650 to 2.5 micron wavelength.

13. The method according to claim 1, wherein the imaging is carried out using infrared thermal imaging in a 2.5 to 18 micron wavelength.

14. The method according to claim 1, wherein the imaging is carried out using visible light surface photographic imaging under magnification.

15. The method according to claim 1, wherein the imaging is carried out using OCT imaging focused on a depth of 2 to 4 mm.

16. The method according to claim 15, wherein the focus is fixed.

17. The method according to claim 15, wherein the focus is variable.

18. The method according to claim 15, wherein the imaging is carried out using at least one of an A-scan, a B-scan and a C-scan.

19. The method according to claim 1, wherein the imaging is carried out using trans-illumination photography.

20. The method according to claim 19, wherein the trans-illumination is produced by oblique illumination of the eyelid from an anterior surface thereof.

21. The method according to claim 19, wherein the trans-illumination is produced by lighting the eyelid from a posterior surface thereof.

22. The method of claim 1,
    wherein the imaging is carried out using trans-illumination photography; and
    wherein the imaging is carried out by scanning a surface that is trans-illuminated and processing resulting scanned images to produce a single image.

23. The method of claim 22, wherein the imaging at least a portion of the central duct of the at least one meibomian gland comprises imaging the central duct.

24. The method of claim 22, wherein the imaging at least a portion of the central duct of the at least one meibomian gland comprises imaging at least one acinus.

25. The method of claim 22, wherein the imaging at least a portion of the central duct of the at least one meibomian gland comprises imaging the central duct and at least one acinus to allow visualization of whether secretory material flows from the at least one acinus to the central duct when a force is applied to the eyelid.

26. A method of evaluating dry eye wherein the flow of naturally occurring secretion to the eye is reduced or stopped due to the presence of an obstruction of a meibomian gland in an eyelid having a plurality of meibomian glands comprising:
  imaging at least one meibomian gland of the plurality of meibomian glands to diagnose a condition of the at least one meibomian gland; and
  wherein the imaging comprises imaging of at least a portion of a central duct of the at least one meibomian gland that is located below an orifice of the at least one meibomian gland to determine if there is an obstruction in the central duct of the meibomian gland and applying force to the eyelid; wherein the imaging is carried out with the force applied to the eyelid.

27. The method of claim 26, wherein the imaging is carried out with the force applied to the eyelid as a result of natural blinking of the eyelid.

28. The method of claim 26, wherein the imaging is carried out with the force applied to the eyelid that mimics pressure applied during blinking of the eyelid.

29. The method of claim 26, wherein the imaging further comprises imaging of the at least a portion of the central duct of the at least one meibomian gland when the force is applied to the eyelid.

30. The method of claim 26, further comprising:
  treating the at least one meibomian gland to remove an obstruction from at least a portion of a central duct of the at least one meibomian gland located below an orifice of the at least one meibomian gland; and
  re-imaging the at least one meibomian gland to verify that the obstruction has been removed.

31. The method of claim 26, wherein the imaging is carried out using at least one of VHF ultrasound imaging, OCT imaging, NIR optical imaging, infrared thermal imaging, trans-illumination imaging, and visible light photographic imaging of a surface of the eyelid.

32. The method of claim 26, wherein imaging at least a portion of the central duct of the at least one meibomian gland comprises imaging the central duct.

33. The method of claim 26, wherein imaging at least a portion of the central duct of the at least one meibomian gland comprises imaging at least one acinus.

34. The method of claim 26, wherein imaging at least a portion of the central duct of the at least one meibomian gland comprises imaging the central duct and at least one acinus to allow visualization of whether secretory material flows from the at least one acinus to the central duct when the force is applied to the eyelid.

35. A method of evaluating dry eye wherein the flow of naturally occurring secretion to the eye is reduced or stopped due to the presence of an obstruction of a meibomian gland in an eyelid having a plurality of meibomian glands comprising:
  imaging at least one meibomian gland of the plurality of meibomian glands to diagnose a condition of the at least one meibomian gland;
  wherein the imaging comprises imaging of at least a portion of a central duct of the at least one meibomian gland that is located below an orifice of the at least one meibomian gland to determine if there is an obstruction in the central duct of the meibomian gland; and
  wherein the imaging at least a portion of the central duct of the at least one meibomian gland comprises imaging the central duct and at least one acinus to determine if there is an obstruction in the at least one acinus or at a junction of the central duct and the at least one acinus.

36. A method of evaluating dry eye wherein the flow of naturally occurring secretion to the eye is reduced or stopped due to the presence of an obstruction of a meibomian gland in an eyelid having a plurality of meibomian glands comprising:
  imaging at least one meibomian gland of the plurality of meibomian glands to diagnose a condition of the at least one meibomian gland;
  wherein the imaging comprises imaging of at least a portion of a central duct of the at least one meibomian gland that is located below an orifice of the at least one meibomian gland to determine if there is an obstruction in the central duct of the meibomian gland; and
  wherein the imaging is carried out using visible light surface photographic imaging under magnification.

37. A method of evaluating dry eye wherein the flow of naturally occurring secretion to the eye is reduced or stopped due to the presence of an obstruction of a meibomian gland in an eyelid having a plurality of meibomian glands comprising:
  imaging at least one meibomian gland of the plurality of meibomian glands to diagnose a condition of the at least one meibomian gland;
  wherein the imaging comprises imaging of at least a portion of a central duct of the at least one meibomian gland that is located below an orifice of the at least one meibomian gland to determine if there is an obstruction in the central duct of the meibomian gland;
  wherein the imaging is carried out using trans-illumination photography; and
  wherein the trans-illumination is produced by lighting the eyelid from a posterior surface thereof.

38. A method of evaluating dry eye wherein the flow of naturally occurring secretion to the eye is reduced or stopped due to the presence of an obstruction of a meibomian gland in an eyelid having a plurality of meibomian glands comprising:
  imaging at least one meibomian gland of the plurality of meibomian glands to diagnose a condition of the at least one meibomian gland;
  wherein the imaging comprises imaging of at least a portion of a central duct of the at least one meibomian gland that is located below an orifice of the at least one meibomian gland to determine if there is an obstruction in the central duct of the meibomian gland; and
  wherein the imaging at least a portion of the central duct of the at least one meibomian gland comprises imaging the central duct and at least one acinus to allow visualization of whether secretory material flows from the at least one acinus to the central duct when a force is applied to the eyelid.

* * * * *